(12) United States Patent
Shin

(10) Patent No.: US 7,745,393 B2
(45) Date of Patent: Jun. 29, 2010

(54) MINIMALIST BZIP PROTEINS AND USES THEREOF

(76) Inventor: Jumi Shin, 91 Compass Way, Mississauga, Ontario (CA) L5G 4T8

(*) Notice: Subject to any disclaimer, the term of this patent is extended or adjusted under 35 U.S.C. 154(b) by 117 days.

(21) Appl. No.: 11/592,186

(22) Filed: Nov. 3, 2006

(65) Prior Publication Data

US 2007/0141672 A1 Jun. 21, 2007

Related U.S. Application Data

(60) Provisional application No. 60/732,700, filed on Nov. 3, 2005.

(51) Int. Cl.
*C07K 14/00* (2006.01)
(52) U.S. Cl. .......................................... 514/2; 530/300
(58) Field of Classification Search ....................... None
See application file for complete search history.

(56) References Cited

U.S. PATENT DOCUMENTS

| 5,962,271 | A | 10/1999 | Chenchik |
| 5,962,272 | A | 10/1999 | Chenchik |
| 6,410,246 | B1 | 6/2002 | Zhu |
| 6,410,271 | B1 | 6/2002 | Zhu |
| 2007/0009938 | A1 | 1/2007 | Shin |

OTHER PUBLICATIONS

Lajmi et al.,"Short, Hydrophobic, Alanine-Based Proteins based on the Basic Region/Leucine Zipper Protein Motif: Overcoming inclusion body formation and protein aggregation during overexpression, purification, and renaturation", Protein Expression and Purification 18: 394-403 (2000).*
Glover and Harrison, "Crystal structure of the heterodimeric bZIP transcription factor c-Fos-c-Jun bound to DNA", Nature 373: 275-261 (1995).*
Grinberg and Kerppola, "Both Max and TFE3 cooperate with Smad proteins to bind the Plasminogen Activator Inhibitor-1 Promoter, but they have opposite effects on transcriptional activity", The Journal of Biological Chemistry 278(13): 11227-11236 (2003).*
"BD Matchmaker™ One-Hybrid Library Construction & Screening Kit", BD Biosciences Clontech, Clontechniques, Jan. 2003.
Shin, J. A., "bZIP/bHLH hybrid proteins target specific DNA sequences", The 229th ACS National Meeting, 2005, abstract submitted Nov. 2004, San Diego, CA, USA, abstract.
Shin, J. A., et al., "In vivo directed evolution of DNA-binding proteins in yeast", The 229th ACS National Meeting, 2005, abstract submitted Nov. 2004, San Diego, CA, USA, abstract.

Shin, J. A., "A New Protein-DNA Interaction: designed proteins target the E-box", The 229th ACS National Meeting, 2005, San Diego, CA, USA, poster presentation.
Shin, J. A., "A New Protein-DNA Interaction: designed proteins target the E-box", Canadian Society of Chemistry Meeting, 2005, Saskatoon, Canada, poster presentation.
Ferré-D'Amaré, A.R., et al., "Structure and function of the b/HLH/Z domain of USF", The EMBO Journal, 1994, pp. 180-189, vol. 13, No. 1.
Jakoby, M., et al., "bZIP transcription factors in *Arabidopsis*", Trends in Plant Science, Mar. 2002, pp. 106-111, vol. 7, No. 3.
Nair, S.K. and Burley, S.K., X-Ray Structures of Myc-Max and Mad-Max Recognizing DNA: Molecular Bases of Regulation by Proto-Oncogenic Transcription Factors, Cell, 2003, pp. 193-205, vol. 112.
Lavigne, P., et al., "Insights into the Mechanism of Heterodimerization from the $^1$H-NMR Solution Structure of the c-Myc-Max Heterodimeric Leucine Zipper", Journal of Molecular Biology, 1998, pp. 165-181, vol. 281.
Ferré-D'Amaré, A.R., et al., "Recognition by Max of its cognate DNA through a dimeric b/HLH/Z domain", Nature, 1993, pp. 38-45, vol. 363.
Selvaraj, S., et al., "Specificity of Protein—DNA Recognition Revealed by Structure-based Potentials: Symmetric/Asymmetric and Cognate/Non-cognate Binding", Journal of Molecular Biology, 2002, pp. 907-915, vol. 322.
Agre, P., et al., "Cognate DNA Binding Specificity Retained After Leucine Zipper Exchange Between GCN4 and C/EBP", Science, 1989, pp. 922-926, vol. 246.
Johnson, O.L., and Tracy, M., "Peptide and Protein Drug Delivery", Encyclopedia of Controlled Drug Delivery, 1999, pp. 816-833, vol. 2.
Wu, C.Y., et al., "The GCN4 motif in a rice glutelin gene is essential for endosperm-specific gene expression and is activated by Opaque-2 in transgenic rice plants", The Plant Journal, 1998, pp. 673-683, vol. 14, Issue 6.
Kaiser, J., "First Pass at Cancer Genome Reveals Complex Landscape", Science, 2006, p. 1370, vol. 313.
Lajmi, A.R., "Short, Hydrophobic, Alanine-Based Proteins Based on the Basic Region/Leucine Zipper Protein motif: Overcoming Inclusion Body Formation and Protein Aggregation during Overexpression, Purification, and Renaturation", Protein Expression and Purification, 2000, pp. 394-403, vol. 18.
Gura, T., "Systems for Identifying New Drugs Are Often Faulty", Science, 1997, pp. 1041-1042, vol. 278.

* cited by examiner

*Primary Examiner*—Anand U Desai
(74) *Attorney, Agent, or Firm*—Bereskin & Parr LLP; Melanie Szweras

(57) ABSTRACT

The present invention provides minimalist bZIP proteins having a basic region derived from bHLH proteins fused to a leucine zipper dimerization domain derived from bZIP proteins and methods and uses thereof in the treatment of cancer. The present invention also provides pharmaceutical compositions for treating cancer.

31 Claims, 13 Drawing Sheets

--Prior Art--

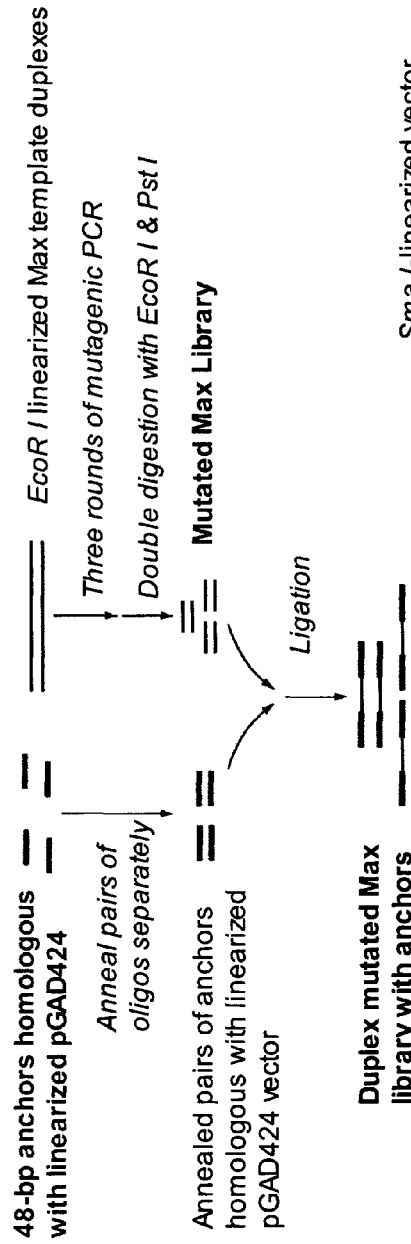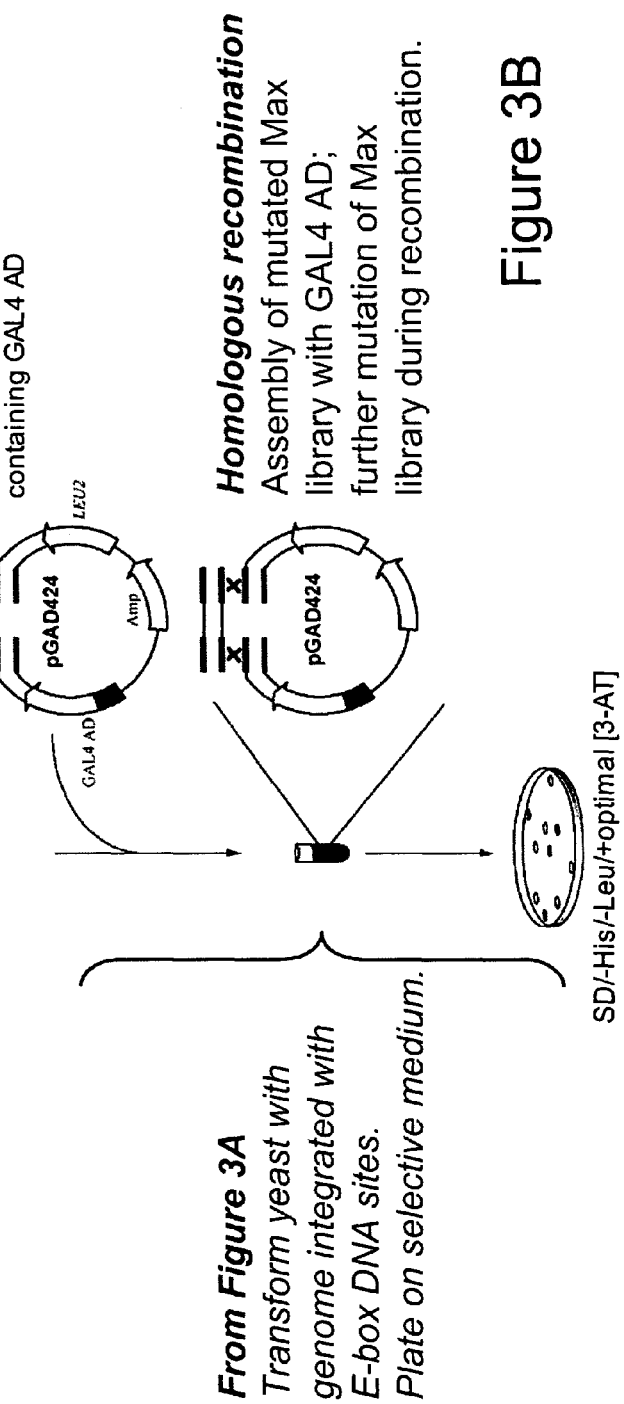
Figure 3B

Native Max bHLHZ control

*basic region*         *helix 1*       *loop*      *helix 2*

```
        30        40        50        60
         |         |         |         |
ADKRAHHNALERKRRDHIKDSFHSLRDSVPSLQGEKASRAQILDKATE
                      leucine zipper
 70        80        90       100       110
  |         |         |         |         |
YIQYMRRKNDTHQQDIDDLKRQNALLEQQVRALEKARSSAQLQT   (SEQ ID NO:55)
```

ArntbHLH-C/EBP

*basic region*         *helix-loop-helix*

```
        90       100       110       120
         |         |         |         |
DQMSNDKERFARENHSEIERRRRNKMTAYITELSDMVPTCSALARKPDK
  130       140
   |         |                  leucine zipper
LTILRMAVSHMKSLRGTRIRLEQKVLELTSDNDRLRKRVEQLSRELDTL  (SEQ ID NO:56)
```

ArntbHLH

*basic region*         *helix-loop-helix*

```
DQMSNDKERFARENHSEIERRRRNKMTAYITELSDMVPTCSALARK
PDKLTILRMAVSHMKSLRGTRIR  (SEQ ID NO:57)
```

Arnt-C/EBP

*basic region*         *helix 1*

```
DQMSNDKERFARENHSEIERRRRNKMTAYITELSRIR
             leucine zipper
LEQKVLELTSDNDRLRKRVEQLSRELDTL  (SEQ ID NO:58)
```

Figure 5

A)
Max-C/EBP (original template for reference)
   *basic region*          *leucine zipper*
ADKRAHHNALERKRRDHIKDSFHSLR-*RIR*-LEQKVLELTSDNDRLRKRVEQLSRELDTL (SEQ ID NO:1)

MM10
ADKTAHHNALERKRRDHIKDSFHSLR-*RIR*-LEQKVLELTSDNDRLRKRVEQLSRELDTL (SEQ ID NO:59)

B)
Max bHLHZ control
 *basic region*    *helix-loop-helix*
ADKRAHHNALERKRR-DHIKDSFHSLRDSVPSLQGEKASRAQILDKATEYIQYM-
  *leucine zipper*
RRKNDTHQQDIDDLKRQNALLEQQVRALEKARSSAQLQT (SEQ ID NO:55)

Max1bHLH-C/EBP (original template for reference)
ADKRAHHNALERKRR-DHIKDSFHSLRDSVPSLQGEKASRAQILDKATEYIQYM-
*RIR*-LEQKVLELTSDNDRLRKRVEQLSRELDTL (SEQ ID NO: 60)

Max-C/EBP Hinge 3 (EYR) or MMbHLH/EYR
ADKRAHHNALERKRR-DHIKDSFHSLRDSVPSLQGEKASRAQILDKATEYIQYM
-*EYR*-TQQKVLELTSDNDRLRKRVEQLSRELDTL (SEQ ID NO:61)

Max-C/EBP (MQQK)
ADKRAHHNALERKRR-DHIKDSFHSLRDSVPSLQGEKASRAQILDKATEYIQY
-MQQK-VLELTSDNDRLRKRVEQLSRELDTL (SEQ ID NO:62)

Max-C/EBP (TQQK)
ADKRAHHNALERKRR-DHIKDSFHSLRDSVPSLQGEKASRAQILDKATEYIQY-
TQQKVLELTSDNDRLRKRVEQLSRELDTL (SEQ ID NO:63)

Max-C/EBP (IQQK)
ADKRAHHNALERKRR-DHIKDSFHSLRDSVPSLQGEKASRAQILDKATEYIQY-IQQK-
VLELTSDNDRLRKRVEQLSRELDTL (SEQ ID NO:64)

Figure 9

SEQUENCE LISTING

```
<160> NUMBER OF SEQ ID NOS: 66

<210> SEQ ID NO 1
<211> LENGTH: 56
<212> TYPE: PRT
<213> ORGANISM: Artificial sequence
<220> FEATURE:
<223> OTHER INFORMATION: fusion protein

<400> SEQUENCE: 1

Ala Asp Lys Arg Ala His His Asn Ala Leu Glu Arg Lys Arg Arg Asp
1               5                   10                  15

His Ile Lys Asp Ser Phe His Ser Arg Ile Arg Leu Glu Gln Lys Val
            20                  25                  30

Leu Glu Leu Thr Ser Asp Asn Asp Arg Leu Arg Lys Arg Val Glu Gln
        35                  40                  45

Leu Ser Arg Glu Leu Asp Thr Leu
    50                  55

<210> SEQ ID NO 2
<211> LENGTH: 57
<212> TYPE: PRT
<213> ORGANISM: Artificial sequence
<220> FEATURE:
<223> OTHER INFORMATION: fusion protein

<400> SEQUENCE: 2

Ala Asp Lys Arg Ala His His Asn Ala Leu Glu Arg Lys Arg Arg Asp
1               5                   10                  15

His Ile Lys Asp Ser Phe His Ser Leu Arg Ile Arg Leu Glu Gln Lys
            20                  25                  30

Val Leu Glu Leu Thr Ser Asp Asn Asp Arg Leu Arg Lys Arg Val Glu
        35                  40                  45

Gln Leu Ser Arg Glu Leu Asp Thr Leu
    50                  55
```

<210> SEQ ID NO 3
<211> LENGTH: 58
<212> TYPE: PRT
<213> ORGANISM: Artificial sequence
<220> FEATURE:
<223> OTHER INFORMATION: fusion protein

<400> SEQUENCE: 3

Ala Asp Lys Arg Ala His His Asn Ala Leu Glu Arg Lys Arg Arg Asp
1               5                   10                  15

His Ile Lys Asp Ser Phe His Ser Leu Arg Arg Ile Arg Leu Glu Gln
            20                  25                  30

Lys Val Leu Glu Leu Thr Ser Asp Asn Asp Arg Leu Arg Lys Arg Val
        35                  40                  45

Glu Gln Leu Ser Arg Glu Leu Asp Thr Leu
    50                  55

<210> SEQ ID NO 4
<211> LENGTH: 56
<212> TYPE: PRT
<213> ORGANISM: Artificial sequence
<220> FEATURE:
<223> OTHER INFORMATION: fusion protein

<400> SEQUENCE: 4

Ala Asp Lys Arg Ala His His Asn Ala Leu Glu Arg Lys Arg Arg Asp
1               5                   10                  15

His Ile Lys Asp Ser Phe His Ser Gly Ile Arg Leu Glu Gln Lys Val
            20                  25                  30

Leu Glu Leu Thr Ser Asp Asn Asp Arg Leu Arg Lys Arg Val Glu Gln
        35                  40                  45

Leu Ser Arg Glu Leu Asp Thr Leu
    50                  55

<210> SEQ ID NO 5
<211> LENGTH: 57
<212> TYPE: PRT
<213> ORGANISM: Artificial sequence
<220> FEATURE:
<223> OTHER INFORMATION: fusion protein

<400> SEQUENCE: 5

Ala Asp Lys Arg Ala His His Asn Ala Leu Glu Arg Lys Arg Arg Asp
1               5                   10                  15

His Ile Lys Asp Ser Phe His Ser Leu Gly Ile Arg Leu Glu Gln Lys
            20                  25                  30

Val Leu Glu Leu Thr Ser Asp Asn Asp Arg Leu Arg Lys Arg Val Glu
        35                  40                  45

Gln Leu Ser Arg Glu Leu Asp Thr Leu
    50                  55

<210> SEQ ID NO 6
<211> LENGTH: 58
<212> TYPE: PRT
<213> ORGANISM: Artificial sequence
<220> FEATURE:
<223> OTHER INFORMATION: fusion protein

<400> SEQUENCE: 6

Ala Asp Lys Arg Ala His His Asn Ala Leu Glu Arg Lys Arg Arg Asp
1               5                   10                  15

His Ile Lys Asp Ser Phe His Ser Leu Arg Gly Ile Arg Leu Glu Gln
            20                  25                  30

Lys Val Leu Glu Leu Thr Ser Asp Asn Asp Arg Leu Arg Lys Arg Val
        35                  40                  45

Glu Gln Leu Ser Arg Glu Leu Asp Thr Leu
    50                  55

<210> SEQ ID NO 7
<211> LENGTH: 71
<212> TYPE: PRT
<213> ORGANISM: Artificial sequence
<220> FEATURE:
<223> OTHER INFORMATION: fusion protein

<400> SEQUENCE: 7

Lys Phe Leu Arg Cys Asp Asp Gln Met Ser Asn Asp Lys Glu Arg
1               5                   10                  15

Phe Ala Arg Glu Asn His Ser Glu Ile Glu Arg Arg Arg Asn Lys
            20                  25                  30

Met Thr Ala Tyr Ile Thr Glu Arg Ile Arg Leu Glu Gln Lys Val Leu
        35                  40                  45

Glu Leu Thr Ser Asp Asn Asp Arg Leu Arg Lys Arg Val Glu Gln Leu
    50                  55                  60

Ser Arg Glu Leu Asp Thr Leu
65                  70

<210> SEQ ID NO 8
<211> LENGTH: 72
<212> TYPE: PRT
<213> ORGANISM: Artificial sequence
<220> FEATURE:
<223> OTHER INFORMATION: fusion protein

<400> SEQUENCE: 8

Lys Phe Leu Arg Cys Asp Asp Gln Met Ser Asn Asp Lys Glu Arg
1               5                   10                  15

Phe Ala Arg Glu Asn His Ser Glu Ile Glu Arg Arg Arg Asn Lys
            20                  25                  30

Met Thr Ala Tyr Ile Thr Glu Leu Arg Ile Arg Leu Glu Gln Lys Val
        35                  40                  45

Leu Glu Leu Thr Ser Asp Asn Asp Arg Leu Arg Lys Arg Val Glu Gln
    50                  55                  60

Leu Ser Arg Glu Leu Asp Thr Leu
65                  70

<210> SEQ ID NO 9
<211> LENGTH: 73
<212> TYPE: PRT
<213> ORGANISM: Artificial sequence
<220> FEATURE:
<223> OTHER INFORMATION: fusion protein

<400> SEQUENCE: 9

Lys Phe Leu Arg Cys Asp Asp Gln Met Ser Asn Asp Lys Glu Arg
1               5                   10                  15

Phe Ala Arg Glu Asn His Ser Glu Ile Glu Arg Arg Arg Asn Lys
            20                  25                  30

Met Thr Ala Tyr Ile Thr Glu Leu Ser Arg Ile Arg Leu Glu Gln Lys
        35                  40                  45

```
Val Leu Glu Leu Thr Ser Asp Asn Asp Arg Leu Arg Lys Arg Val Glu
 50                  55                  60

Gln Leu Ser Arg Glu Leu Asp Thr Leu
 65                  70

<210> SEQ ID NO 10
<211> LENGTH: 71
<212> TYPE: PRT
<213> ORGANISM: Artificial sequence
<220> FEATURE:
<223> OTHER INFORMATION: fusion protein

<400> SEQUENCE: 10

Lys Phe Leu Arg Cys Asp Asp Asp Gln Met Ser Asn Asp Lys Glu Arg
 1               5                  10                  15

Phe Ala Arg Glu Asn His Ser Glu Ile Glu Arg Arg Arg Asn Lys
                 20                  25                  30

Met Thr Ala Tyr Ile Thr Glu Gly Ile Arg Leu Glu Gln Lys Val Leu
             35                  40                  45

Glu Leu Thr Ser Asp Asn Asp Arg Leu Arg Lys Arg Val Glu Gln Leu
 50                  55                  60

Ser Arg Glu Leu Asp Thr Leu
 65                  70

<210> SEQ ID NO 11
<211> LENGTH: 72
<212> TYPE: PRT
<213> ORGANISM: Artificial sequence
<220> FEATURE:
<223> OTHER INFORMATION: fusion protein

<400> SEQUENCE: 11

Lys Phe Leu Arg Cys Asp Asp Asp Gln Met Ser Asn Asp Lys Glu Arg
 1               5                  10                  15

Phe Ala Arg Glu Asn His Ser Glu Ile Glu Arg Arg Arg Arg Asn Lys
                 20                  25                  30

Met Thr Ala Tyr Ile Thr Glu Leu Gly Ile Arg Leu Glu Gln Lys Val
             35                  40                  45

Leu Glu Leu Thr Ser Asp Asn Asp Arg Leu Arg Lys Arg Val Glu Gln
 50                  55                  60

Leu Ser Arg Glu Leu Asp Thr Leu
 65                  70

<210> SEQ ID NO 12
<211> LENGTH: 73
<212> TYPE: PRT
<213> ORGANISM: Artificial sequence
<220> FEATURE:
<223> OTHER INFORMATION: fusion protein

<400> SEQUENCE: 12

Lys Phe Leu Arg Cys Asp Asp Asp Gln Met Ser Asn Asp Lys Glu Arg
 1               5                  10                  15

Phe Ala Arg Glu Asn His Ser Glu Ile Glu Arg Arg Arg Arg Asn Lys
                 20                  25                  30

Met Thr Ala Tyr Ile Thr Glu Leu Ser Gly Ile Arg Leu Glu Gln Lys
             35                  40                  45

Val Leu Glu Leu Thr Ser Asp Asn Asp Arg Leu Arg Lys Arg Val Glu
 50                  55                  60

Gln Leu Ser Arg Glu Leu Asp Thr Leu
```

<210> SEQ ID NO 13
<211> LENGTH: 66
<212> TYPE: PRT
<213> ORGANISM: Artificial sequence
<220> FEATURE:
<223> OTHER INFORMATION: fusion protein

<400> SEQUENCE: 13

Ser Asn Glu Tyr Arg Val Arg Arg Glu Arg Asn Asn Ile Ala Val Arg
1               5                   10                  15

Lys Ser Arg Asp Lys Ala Lys Gln Arg Asn Val Glu Leu Glu Ala Glu
            20                  25                  30

Thr Asp Gln Leu Glu Asp Glu Lys Ser Ala Leu Gln Thr Glu Ile Ala
        35                  40                  45

Asn Leu Leu Lys Glu Lys Glu Lys Leu Glu Phe Ile Leu Ala Ala His
    50                  55                  60

Arg Pro
65

<210> SEQ ID NO 14
<211> LENGTH: 62
<212> TYPE: PRT
<213> ORGANISM: Artificial sequence
<220> FEATURE:
<223> OTHER INFORMATION: fusion protein

<400> SEQUENCE: 14

Ala Asp Lys Arg Ala His His Asn Ala Leu Glu Arg Lys Arg Arg Asp
1               5                   10                  15

His Ile Lys Asp Ser Phe His Ser Leu Glu Glu Lys Val Lys Thr Leu
            20                  25                  30

Lys Ala Gln Asn Ser Glu Leu Ala Ser Thr Ala Asn Met Leu Arg Glu
        35                  40                  45

Gln Val Ala Gln Leu Lys Gln Lys Val Met Asn His Val Asn
    50                  55                  60

<210> SEQ ID NO 15
<211> LENGTH: 63
<212> TYPE: PRT
<213> ORGANISM: Artificial sequence
<220> FEATURE:
<223> OTHER INFORMATION: fusion protein

<400> SEQUENCE: 15

Ala Asp Lys Arg Ala His His Asn Ala Leu Glu Arg Lys Arg Arg Asp
1               5                   10                  15

His Ile Lys Asp Ser Phe His Ser Leu Leu Glu Glu Lys Val Lys Thr
            20                  25                  30

Leu Lys Ala Gln Asn Ser Glu Leu Ala Ser Thr Ala Asn Met Leu Arg
        35                  40                  45

Glu Gln Val Ala Gln Leu Lys Gln Lys Val Met Asn His Val Asn
    50                  55                  60

<210> SEQ ID NO 16
<211> LENGTH: 64
<212> TYPE: PRT
<213> ORGANISM: Artificial sequence
<220> FEATURE:
<223> OTHER INFORMATION: fusion protein

<400> SEQUENCE: 16

Ala Asp Lys Arg Ala His His Asn Ala Leu Glu Arg Lys Arg Arg Asp
1               5                   10                  15

His Ile Lys Asp Ser Phe His Ser Leu Arg Leu Glu Glu Lys Val Lys
                20                  25                  30

Thr Leu Lys Ala Gln Asn Ser Glu Leu Ala Ser Thr Ala Asn Met Leu
            35                  40                  45

Arg Glu Gln Val Ala Gln Leu Lys Gln Lys Val Met Asn His Val Asn
        50                  55                  60

<210> SEQ ID NO 17
<211> LENGTH: 77
<212> TYPE: PRT
<213> ORGANISM: Artificial sequence
<220> FEATURE:
<223> OTHER INFORMATION: fusion protein

<400> SEQUENCE: 17

Ala Ser Arg Lys Arg Arg Lys Pro Val Gln Lys Thr Val Lys Pro Ile
1               5                   10                  15

Pro Ala Glu Gly Ile Lys Ser Asn Pro Ser Lys Arg His Arg Asp Arg
                20                  25                  30

Leu Asn Thr Glu Leu Asp Arg Leu Glu Ala Glu Thr Asp Gln Leu Glu
            35                  40                  45

Asp Glu Lys Ser Ala Leu Gln Thr Glu Ile Ala Asn Leu Leu Lys Glu
        50                  55                  60

Lys Glu Lys Leu Glu Phe Ile Leu Ala Ala His Arg Pro
65                  70                  75

<210> SEQ ID NO 18
<211> LENGTH: 78
<212> TYPE: PRT
<213> ORGANISM: Artificial sequence
<220> FEATURE:
<223> OTHER INFORMATION: fusion protein

<400> SEQUENCE: 18

Ala Ser Arg Lys Arg Arg Lys Pro Val Gln Lys Thr Val Lys Pro Ile
1               5                   10                  15

Pro Ala Glu Gly Ile Lys Ser Asn Pro Ser Lys Arg His Arg Asp Arg
                20                  25                  30

Leu Asn Thr Glu Leu Asp Arg Leu Leu Glu Ala Glu Thr Asp Gln Leu
            35                  40                  45

Glu Asp Glu Lys Ser Ala Leu Gln Thr Glu Ile Ala Asn Leu Leu Lys
        50                  55                  60

Glu Lys Glu Lys Leu Glu Phe Ile Leu Ala Ala His Arg Pro
65                  70                  75

<210> SEQ ID NO 19
<211> LENGTH: 79
<212> TYPE: PRT
<213> ORGANISM: Artificial sequence
<220> FEATURE:
<223> OTHER INFORMATION: fusion protein

<400> SEQUENCE: 19

Ala Ser Arg Lys Arg Arg Lys Pro Val Gln Lys Thr Val Lys Pro Ile
1               5                   10                  15

Pro Ala Glu Gly Ile Lys Ser Asn Pro Ser Lys Arg His Arg Asp Arg
                20                  25                  30

-continued

Leu Asn Thr Glu Leu Asp Arg Leu Ala Leu Glu Ala Glu Thr Asp Gln
         35                  40                  45

Leu Glu Asp Glu Lys Ser Ala Leu Gln Thr Glu Ile Ala Asn Leu Leu
 50                  55                  60

Lys Glu Lys Glu Lys Leu Glu Phe Ile Leu Ala Ala His Arg Pro
65                  70                  75

<210> SEQ ID NO 20
<211> LENGTH: 77
<212> TYPE: PRT
<213> ORGANISM: Artificial sequence
<220> FEATURE:
<223> OTHER INFORMATION: fusion protein

<400> SEQUENCE: 20

Lys Phe Leu Arg Cys Asp Asp Gln Met Ser Asn Asp Lys Glu Arg
1               5                   10                  15

Phe Ala Arg Glu Asn His Ser Glu Ile Glu Arg Arg Arg Asn Lys
             20                  25                  30

Met Thr Ala Tyr Ile Thr Glu Leu Glu Glu Lys Val Lys Thr Leu Lys
         35                  40                  45

Ala Gln Asn Ser Glu Leu Ala Ser Thr Ala Asn Met Leu Arg Glu Gln
 50                  55                  60

Val Ala Gln Leu Lys Gln Lys Val Met Asn His Val Asn
65                  70                  75

<210> SEQ ID NO 21
<211> LENGTH: 78
<212> TYPE: PRT
<213> ORGANISM: Artificial sequence
<220> FEATURE:
<223> OTHER INFORMATION: fusion protein

<400> SEQUENCE: 21

Lys Phe Leu Arg Cys Asp Asp Gln Met Ser Asn Asp Lys Glu Arg
1               5                   10                  15

Phe Ala Arg Glu Asn His Ser Glu Ile Glu Arg Arg Arg Asn Lys
             20                  25                  30

Met Thr Ala Tyr Ile Thr Glu Leu Leu Glu Glu Lys Val Lys Thr Leu
         35                  40                  45

Lys Ala Gln Asn Ser Glu Leu Ala Ser Thr Ala Asn Met Leu Arg Glu
 50                  55                  60

Gln Val Ala Gln Leu Lys Gln Lys Val Met Asn His Val Asn
65                  70                  75

<210> SEQ ID NO 22
<211> LENGTH: 79
<212> TYPE: PRT
<213> ORGANISM: Artificial sequence
<220> FEATURE:
<223> OTHER INFORMATION: fusion protein

<400> SEQUENCE: 22

Lys Phe Leu Arg Cys Asp Asp Gln Met Ser Asn Asp Lys Glu Arg
1               5                   10                  15

Phe Ala Arg Glu Asn His Ser Glu Ile Glu Arg Arg Arg Asn Lys
             20                  25                  30

Met Thr Ala Tyr Ile Thr Glu Leu Ser Leu Glu Glu Lys Val Lys Thr
         35                  40                  45

```
Leu Lys Ala Gln Asn Ser Glu Leu Ala Ser Thr Ala Asn Met Leu Arg
        50                  55                  60

Glu Gln Val Ala Gln Leu Lys Gln Lys Val Met Asn His Val Asn
65                  70                  75
```

<210> SEQ ID NO 23
<211> LENGTH: 77
<212> TYPE: PRT
<213> ORGANISM: Artificial sequence
<220> FEATURE:
<223> OTHER INFORMATION: AhR bHLH amino acid sequence

<400> SEQUENCE: 23

```
Ala Ser Arg Lys Arg Arg Lys Pro Val Gln Lys Thr Val Lys Pro Ile
1               5                   10                  15

Pro Ala Glu Gly Ile Lys Ser Asn Pro Ser Lys Arg His Arg Asp Arg
            20                  25                  30

Leu Asn Thr Glu Leu Asp Arg Leu Ala Ser Leu Leu Pro Phe Pro Gln
        35                  40                  45

Asp Val Ile Asn Lys Leu Asp Lys Leu Ser Val Leu Arg Leu Ser Val
    50                  55                  60

Thr Tyr Leu Arg Ala Lys Ser Phe Phe Asp Val Ala Leu
65                  70                  75
```

<210> SEQ ID NO 24
<211> LENGTH: 77
<212> TYPE: PRT
<213> ORGANISM: Artificial sequence
<220> FEATURE:
<223> OTHER INFORMATION: Arnt bHLH amino acid sequence

<400> SEQUENCE: 24

```
Lys Phe Leu Arg Cys Asp Asp Gln Met Ser Asn Asp Lys Glu Arg
1               5                   10                  15

Phe Ala Arg Glu Asn His Ser Glu Ile Glu Arg Arg Arg Asn Lys
            20                  25                  30

Met Thr Ala Tyr Ile Thr Glu Leu Ser Asp Met Val Pro Thr Cys Ser
        35                  40                  45

Ala Leu Ala Arg Lys Pro Asp Lys Leu Thr Ile Leu Arg Met Ala Val
    50                  55                  60

Ser His Met Lys Ser Leu Arg Gly Thr Gly Asn Thr Ser
65                  70                  75
```

<210> SEQ ID NO 25
<211> LENGTH: 64
<212> TYPE: PRT
<213> ORGANISM: Artificial sequence
<220> FEATURE:
<223> OTHER INFORMATION: Fos bZIP amino acid sequence

<400> SEQUENCE: 25

```
Lys Arg Arg Ile Arg Arg Glu Arg Asn Lys Met Ala Ala Ala Lys Cys
1               5                   10                  15

Arg Asn Arg Arg Arg Glu Leu Thr Asp Thr Leu Gln Ala Glu Thr Asp
            20                  25                  30

Gln Leu Glu Asp Glu Lys Ser Ala Leu Gln Thr Glu Ile Ala Asn Leu
        35                  40                  45

Leu Lys Glu Lys Glu Lys Leu Glu Phe Ile Leu Ala Ala His Arg Pro
    50                  55                  60
```

<210> SEQ ID NO 26
<211> LENGTH: 64
<212> TYPE: PRT
<213> ORGANISM: Artificial sequence
<220> FEATURE:
<223> OTHER INFORMATION: Jun bZIP amino acid sequence

<400> SEQUENCE: 26

```
Lys Ala Glu Arg Lys Arg Met Arg Asn Arg Ile Ala Ala Ser Lys Cys
1               5                   10                  15

Arg Lys Arg Lys Leu Glu Arg Ile Ala Arg Leu Glu Glu Lys Val Lys
            20                  25                  30

Thr Leu Lys Ala Gln Asn Ser Glu Leu Ala Ser Thr Ala Asn Met Leu
        35                  40                  45

Arg Glu Gln Val Ala Gln Leu Lys Gln Lys Val Met Asn His Val Asn
    50                  55                  60
```

<210> SEQ ID NO 27
<211> LENGTH: 15
<212> TYPE: PRT
<213> ORGANISM: Artificial sequence
<220> FEATURE:
<223> OTHER INFORMATION: Max basic region (partial)

<400> SEQUENCE: 27

```
Ala Asp Lys Arg Ala His His Asn Ala Leu Glu Arg Lys Arg Arg
1               5                   10                  15
```

<210> SEQ ID NO 28
<211> LENGTH: 15
<212> TYPE: PRT
<213> ORGANISM: Artificial sequence
<220> FEATURE:
<223> OTHER INFORMATION: Myc basic region (partial)

<400> SEQUENCE: 28

```
Asn Val Lys Arg Arg Thr His Asn Val Leu Glu Arg Gln Arg Arg
1               5                   10                  15
```

<210> SEQ ID NO 29
<211> LENGTH: 15
<212> TYPE: PRT
<213> ORGANISM: Artificial sequence
<220> FEATURE:
<223> OTHER INFORMATION: USF basic region (partial)

<400> SEQUENCE: 29

```
Glu Lys Arg Arg Ala Gln His Asn Glu Val Glu Arg Arg Arg Arg
1               5                   10                  15
```

<210> SEQ ID NO 30
<211> LENGTH: 15
<212> TYPE: PRT
<213> ORGANISM: Artificial sequence
<220> FEATURE:
<223> OTHER INFORMATION: TFE3 basic region (partial)

<400> SEQUENCE: 30

```
Arg Gln Lys Lys Asp Asn His Asn Leu Ile Glu Arg Arg Arg Arg
1               5                   10                  15
```

<210> SEQ ID NO 31
<211> LENGTH: 15
<212> TYPE: PRT
<213> ORGANISM: Artificial sequence
<220> FEATURE:

```
<223> OTHER INFORMATION: TFEB basic region (partial)

<400> SEQUENCE: 31

Arg Gln Lys Lys Asp Asn His Asn Leu Ile Glu Arg Arg Arg Arg
1               5                   10                  15

<210> SEQ ID NO 32
<211> LENGTH: 15
<212> TYPE: PRT
<213> ORGANISM: Artificial sequence
<220> FEATURE:
<223> OTHER INFORMATION: Arnt basic region (partial)

<400> SEQUENCE: 32

Arg Phe Ala Arg Glu Asn His Ser Glu Ile Glu Arg Arg Arg Arg
1               5                   10                  15

<210> SEQ ID NO 33
<211> LENGTH: 15
<212> TYPE: PRT
<213> ORGANISM: Artificial sequence
<220> FEATURE:
<223> OTHER INFORMATION: MyoD basic region (partial)

<400> SEQUENCE: 33

Ala Asp Arg Arg Lys Ala Ala Thr Met Arg Glu Arg Arg Arg Leu
1               5                   10                  15

<210> SEQ ID NO 34
<211> LENGTH: 15
<212> TYPE: PRT
<213> ORGANISM: Artificial sequence
<220> FEATURE:
<223> OTHER INFORMATION: E47 basic region (partial)

<400> SEQUENCE: 34

Arg Glu Arg Arg Met Ala Asn Asn Ala Arg Glu Arg Val Arg Val
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: AP4 basic region (partial)

<400> SEQUENCE: 35

Arg Ile Arg Arg Glu Ile Ala Asn Ser Asn Glu Arg Arg Arg Met
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: E12 basic region (partial)

<400> SEQUENCE: 36

Lys Glu Arg Arg Val Ala Asn Asn Ala Arg Glu Arg Leu Arg Val
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Tal1 basic region (partial)
```

```
<400> SEQUENCE: 37

Val Val Arg Arg Ile Phe Thr Asn Ser Arg Glu Arg Trp Arg Gln
1               5                   10                  15

<210> SEQ ID NO 38
<211> LENGTH: 18
<212> TYPE: PRT
<213> ORGANISM: Artificial sequence
<220> FEATURE:
<223> OTHER INFORMATION: AhR basic region (partial)

<400> SEQUENCE: 38

Lys Pro Ile Pro Ala Glu Gly Ile Lys Ser Asn Pro Ser Lys Arg His
1               5                   10                  15

Arg Asp

<210> SEQ ID NO 39
<211> LENGTH: 14
<212> TYPE: PRT
<213> ORGANISM: Artificial sequnece
<220> FEATURE:
<223> OTHER INFORMATION: Sim basic region (partial)

<400> SEQUENCE: 39

Met Lys Glu Lys Ser Lys Asn Ala Ala Arg Thr Arg Arg Glu
1               5                   10

<210> SEQ ID NO 40
<211> LENGTH: 18
<212> TYPE: PRT
<213> ORGANISM: Artificial sequence
<220> FEATURE:
<223> OTHER INFORMATION: GCN4 basic region (partial)

<400> SEQUENCE: 40

Asp Pro Ala Ala Leu Lys Arg Ala Arg Asn Thr Glu Ala Ala Arg Arg
1               5                   10                  15

Ser Arg

<210> SEQ ID NO 41
<211> LENGTH: 24
<212> TYPE: PRT
<213> ORGANISM: Artificial sequnece
<220> FEATURE:
<223> OTHER INFORMATION: Max basic helix - I

<400> SEQUENCE: 41

Ala Asp Lys Arg Ala His His Asn Ala Leu Glu Arg Lys Arg Arg Asp
1               5                   10                  15

His Ile Lys Asp Ser Phe His Ser
            20

<210> SEQ ID NO 42
<211> LENGTH: 24
<212> TYPE: PRT
<213> ORGANISM: Artificial sequence
<220> FEATURE:
<223> OTHER INFORMATION: Max mutant basic helix - I

<400> SEQUENCE: 42

Ala Ala Lys Arg Ala Ala His Asn Ala Ala Glu Arg Ala Arg Arg Ala
1               5                   10                  15

Ala Ala Ala Ala Ala Ala Ala Ala
```

<210> SEQ ID NO 43
<211> LENGTH: 39
<212> TYPE: PRT
<213> ORGANISM: Artificial sequence
<220> FEATURE:
<223> OTHER INFORMATION: Arnt basic helix - I

<400> SEQUENCE: 43

```
Lys Phe Leu Arg Cys Asp Asp Gln Met Ser Asn Asp Lys Glu Arg
1               5                   10                  15

Leu Ala Arg Glu Asn His Ser Glu Ile Glu Arg Arg Arg Asn Lys
                20                  25                  30

Met Thr Ala Tyr Ile Thr Glu
            35
```

<210> SEQ ID NO 44
<211> LENGTH: 24
<212> TYPE: PRT
<213> ORGANISM: Artificial sequence
<220> FEATURE:
<223> OTHER INFORMATION: Arnt mutant basic helix - I

<400> SEQUENCE: 44

```
Ala Ala Ala Arg Ala Ala His Ser Ala Ala Glu Arg Ala Arg Ala
1               5                   10                  15

Ala Ala Ala Ala Ala Ala Ala Ala
                20
```

<210> SEQ ID NO 45
<211> LENGTH: 39
<212> TYPE: PRT
<213> ORGANISM: Artificial sequence
<220> FEATURE:
<223> OTHER INFORMATION: AhR basic helix - I

<400> SEQUENCE: 45

```
Ala Ser Arg Lys Arg Arg Lys Pro Val Gln Lys Thr Val Lys Pro Ile
1               5                   10                  15

Pro Ala Glu Gly Ile Lys Ser Asn Pro Ser Lys Arg His Arg Asp Arg
                20                  25                  30

Leu Asn Thr Glu Leu Asp Arg
            35
```

<210> SEQ ID NO 46
<211> LENGTH: 24
<212> TYPE: PRT
<213> ORGANISM: Artificial sequence
<220> FEATURE:
<223> OTHER INFORMATION: AhR mutant basic helix - I

<400> SEQUENCE: 46

```
Ala Ala Ala Ala Ala Ala Ala Ala Ala Pro Ser Lys Arg His Arg Ala
1               5                   10                  15

Ala Ala Ala Ala Ala Ala Ala Ala
                20
```

<210> SEQ ID NO 47
<211> LENGTH: 28
<212> TYPE: PRT
<213> ORGANISM: Artificial sequence
<220> FEATURE:
<223> OTHER INFORMATION: C/EBP bZIP

```
<400> SEQUENCE: 47

Ser Asn Glu Tyr Arg Val Arg Arg Glu Arg Asn Asn Ile Ala Val Arg
1               5                   10                  15

Lys Ser Arg Asp Lys Ala Lys Gln Arg Asn Val Glu
            20                  25

<210> SEQ ID NO 48
<211> LENGTH: 28
<212> TYPE: PRT
<213> ORGANISM: Artificial sequence
<220> FEATURE:
<223> OTHER INFORMATION: C/EBP mutant bZIP

<400> SEQUENCE: 48

Ala Ala Ala Ala Ala Ala Ala Arg Ala Arg Asn Asn Ala Ala Val Arg
1               5                   10                  15

Lys Ser Arg Ala Ala Ala Ala Ala Ala Ala Ala Ala
            20                  25

<210> SEQ ID NO 49
<211> LENGTH: 27
<212> TYPE: PRT
<213> ORGANISM: Artificial sequence
<220> FEATURE:
<223> OTHER INFORMATION: GCN4 bZIP

<400> SEQUENCE: 49

Asp Pro Ala Ala Leu Lys Arg Ala Arg Asn Thr Glu Ala Ala Arg Arg
1               5                   10                  15

Ser Arg Ala Arg Lys Leu Gln Arg Met Lys Gln
            20                  25

<210> SEQ ID NO 50
<211> LENGTH: 24
<212> TYPE: PRT
<213> ORGANISM: Artificial sequence
<220> FEATURE:
<223> OTHER INFORMATION: MyoD basic helix - I

<400> SEQUENCE: 50

Ala Asp Arg Arg Lys Ala Ala Thr Met Arg Glu Arg Arg Arg Leu Ser
1               5                   10                  15

Lys Val Asn Glu Ala Phe Glu Thr
            20

<210> SEQ ID NO 51
<211> LENGTH: 24
<212> TYPE: PRT
<213> ORGANISM: Artificial sequence
<220> FEATURE:
<223> OTHER INFORMATION: Max mutant basic helix - I

<400> SEQUENCE: 51

Ala Ala Lys Arg Ala Ala His Asn Ala Arg Glu Arg Ala Arg Leu Ala
1               5                   10                  15

Ala Ala Ala Ala Ala Ala Ala Ala
            20

<210> SEQ ID NO 52
<211> LENGTH: 56
<212> TYPE: PRT
<213> ORGANISM: Artificial sequence
<220> FEATURE:
```

<223> OTHER INFORMATION: fusion protein

<400> SEQUENCE: 52

Ala Asp Lys Arg Ala His His Asn Ala Leu Glu Arg Lys Arg Arg Asp
1               5                   10                  15

His Ile Lys Asp Ser Phe His Ser Arg Ile Arg Leu Glu Gln Lys Val
            20                  25                  30

Leu Glu Leu Thr Ser Asp Asn Asp Arg Leu Arg Lys Arg Val Glu Gln
        35                  40                  45

Leu Ser Arg Glu Leu Asp Thr Leu
    50                  55

<210> SEQ ID NO 53
<211> LENGTH: 56
<212> TYPE: PRT
<213> ORGANISM: Artificial sequence
<220> FEATURE:
<223> OTHER INFORMATION: fusion protein

<400> SEQUENCE: 53

Ala Asp Lys Arg Ala His His Asn Ala Ser Glu Arg Lys Arg Arg Asp
1               5                   10                  15

Thr Ser Arg Thr Leu Ser Thr Leu Arg Ile Arg Leu Glu Gln Lys Val
            20                  25                  30

Leu Glu Leu Thr Ser Asp Ser Asp Arg Leu Arg Lys Arg Val Glu Gln
        35                  40                  45

Leu Ser Arg Glu Leu Asp Thr Leu
    50                  55

<210> SEQ ID NO 54
<211> LENGTH: 56
<212> TYPE: PRT
<213> ORGANISM: Artificial sequence
<220> FEATURE:
<223> OTHER INFORMATION: fusion protein

<400> SEQUENCE: 54

Ala Asp Lys Arg Ala His His Asn Ala Ser Glu Arg Lys Arg Arg Asp
1               5                   10                  15

Thr Ser Arg Thr Leu Ser Thr Leu Arg Ile Arg Leu Glu Gln Lys Val
            20                  25                  30

Leu Glu Leu Thr Ser Asp Asn Asp Arg Leu Arg Lys Arg Val Glu Gln
        35                  40                  45

Leu Ser Arg Glu Leu Asp Thr Leu
    50                  55

<210> SEQ ID NO 55
<211> LENGTH: 92
<212> TYPE: PRT
<213> ORGANISM: Artificial sequence
<220> FEATURE:
<223> OTHER INFORMATION: native Max bHLHZ control

<400> SEQUENCE: 55

Ala Asp Lys Arg Ala His His Asn Ala Leu Glu Arg Lys Arg Arg Asp
1               5                   10                  15

His Ile Lys Asp Ser Phe His Ser Leu Arg Asp Ser Val Pro Ser Leu
            20                  25                  30

Gln Gly Glu Lys Ala Ser Arg Ala Gln Ile Leu Asp Lys Ala Thr Glu
        35                  40                  45

Tyr Ile Gln Tyr Met Arg Arg Lys Asn Asp Thr His Gln Gln Asp Ile
            50                  55                  60

Asp Asp Leu Lys Arg Gln Asn Ala Leu Leu Glu Gln Gln Val Arg Ala
 65                  70                  75                  80

Leu Glu Lys Ala Arg Ser Ser Ala Gln Leu Gln Thr
                 85                  90

<210> SEQ ID NO 56
<211> LENGTH: 98
<212> TYPE: PRT
<213> ORGANISM: Artificial sequence
<220> FEATURE:
<223> OTHER INFORMATION: Arnt bHLH-C/EBP

<400> SEQUENCE: 56

Asp Gln Met Ser Asn Asp Lys Glu Arg Phe Ala Arg Glu Asn His Ser
 1               5                  10                  15

Glu Ile Glu Arg Arg Arg Arg Asn Lys Met Thr Ala Tyr Ile Thr Glu
             20                  25                  30

Leu Ser Asp Met Val Pro Thr Cys Ser Ala Leu Ala Arg Lys Pro Asp
         35                  40                  45

Lys Leu Thr Ile Leu Arg Met Ala Val Ser His Met Lys Ser Leu Arg
     50                  55                  60

Gly Thr Arg Ile Arg Leu Glu Gln Lys Val Leu Glu Leu Thr Ser Asp
 65                  70                  75                  80

Asn Asp Arg Leu Arg Lys Arg Val Glu Gln Leu Ser Arg Glu Leu Asp
                 85                  90                  95

Thr Leu

<210> SEQ ID NO 57
<211> LENGTH: 69
<212> TYPE: PRT
<213> ORGANISM: Artificial sequence
<220> FEATURE:
<223> OTHER INFORMATION: Arnt bHLH

<400> SEQUENCE: 57

Asp Gln Met Ser Asn Asp Lys Glu Arg Phe Ala Arg Glu Asn His Ser
 1               5                  10                  15

Glu Ile Glu Arg Arg Arg Arg Asn Lys Met Thr Ala Tyr Ile Thr Glu
             20                  25                  30

Leu Ser Asp Met Val Pro Thr Cys Ser Ala Leu Ala Arg Lys Pro Asp
         35                  40                  45

Lys Leu Thr Ile Leu Arg Met Ala Val Ser His Met Lys Ser Leu Arg
     50                  55                  60

Gly Thr Arg Ile Arg
 65

<210> SEQ ID NO 58
<211> LENGTH: 66
<212> TYPE: PRT
<213> ORGANISM: Artificial sequence
<220> FEATURE:
<223> OTHER INFORMATION: Arnt-C/EBP

<400> SEQUENCE: 58

Asp Gln Met Ser Asn Asp Lys Glu Arg Phe Ala Arg Glu Asn His Ser
 1               5                  10                  15

Glu Ile Glu Arg Arg Arg Arg Asn Lys Met Thr Ala Tyr Ile Thr Glu
             20                  25                  30

```
Leu Ser Arg Ile Arg Leu Glu Gln Lys Val Leu Glu Leu Thr Ser Asp
        35                  40                  45

Asn Asp Arg Leu Arg Lys Arg Val Glu Gln Leu Ser Arg Glu Leu Asp
 50                  55                  60

Thr Leu
65

<210> SEQ ID NO 59
<211> LENGTH: 58
<212> TYPE: PRT
<213> ORGANISM: Artificial sequence
<220> FEATURE:
<223> OTHER INFORMATION: fusion protein

<400> SEQUENCE: 59

Ala Asp Lys Thr Ala His His Asn Ala Leu Glu Arg Lys Arg Arg Asp
  1               5                  10                  15

His Ile Lys Asp Ser Phe His Ser Leu Arg Arg Ile Arg Leu Glu Gln
             20                  25                  30

Lys Val Leu Glu Leu Thr Ser Asp Asn Asp Arg Leu Arg Lys Arg Val
        35                  40                  45

Glu Gln Leu Ser Arg Glu Leu Asp Thr Leu
 50                  55

<210> SEQ ID NO 60
<211> LENGTH: 85
<212> TYPE: PRT
<213> ORGANISM: Artificial sequence
<220> FEATURE:
<223> OTHER INFORMATION: fusion protein

<400> SEQUENCE: 60

Ala Asp Lys Arg Ala His His Asn Ala Leu Glu Arg Lys Arg Arg Asp
  1               5                  10                  15

His Ile Lys Asp Ser Phe His Ser Leu Arg Asp Ser Val Pro Ser Leu
             20                  25                  30

Gln Gly Glu Lys Ala Ser Arg Ala Gln Ile Leu Asp Lys Ala Thr Glu
        35                  40                  45

Tyr Ile Gln Tyr Met Arg Ile Arg Leu Glu Gln Lys Val Leu Glu Leu
 50                  55                  60

Thr Ser Asp Asn Asp Arg Leu Arg Lys Arg Val Glu Gln Leu Ser Arg
65                  70                  75                  80

Glu Leu Asp Thr Leu
                85

<210> SEQ ID NO 61
<211> LENGTH: 85
<212> TYPE: PRT
<213> ORGANISM: Artificial sequence
<220> FEATURE:
<223> OTHER INFORMATION: fusion protein

<400> SEQUENCE: 61

Ala Asp Lys Arg Ala His His Asn Ala Leu Glu Arg Lys Arg Arg Asp
  1               5                  10                  15

His Ile Lys Asp Ser Phe His Ser Leu Arg Asp Ser Val Pro Ser Leu
             20                  25                  30

Gln Gly Glu Lys Ala Ser Arg Ala Gln Ile Leu Asp Lys Ala Thr Glu
        35                  40                  45
```

Tyr Ile Gln Tyr Met Glu Tyr Arg Thr Gln Gln Lys Val Leu Glu Leu
        50                  55                  60

Thr Ser Asp Asn Asp Arg Leu Arg Lys Arg Val Glu Gln Leu Ser Arg
 65                  70                  75                  80

Glu Leu Asp Thr Leu
            85

<210> SEQ ID NO 62
<211> LENGTH: 81
<212> TYPE: PRT
<213> ORGANISM: Artificial sequence
<220> FEATURE:
<223> OTHER INFORMATION: fusion protein

<400> SEQUENCE: 62

Ala Asp Lys Arg Ala His His Asn Ala Leu Glu Arg Lys Arg Arg Asp
 1               5                  10                  15

His Ile Lys Asp Ser Phe His Ser Leu Arg Asp Ser Val Pro Ser Leu
                20                  25                  30

Gln Gly Glu Lys Ala Ser Arg Ala Gln Ile Leu Asp Lys Ala Thr Glu
            35                  40                  45

Tyr Ile Gln Tyr Met Gln Gln Lys Val Leu Glu Leu Thr Ser Asp Asn
        50                  55                  60

Asp Arg Leu Arg Lys Arg Val Glu Gln Leu Ser Arg Glu Leu Asp Thr
 65                  70                  75                  80

Leu

<210> SEQ ID NO 63
<211> LENGTH: 81
<212> TYPE: PRT
<213> ORGANISM: Artificial sequence
<220> FEATURE:
<223> OTHER INFORMATION: fusion protein

<400> SEQUENCE: 63

Ala Asp Lys Arg Ala His His Asn Ala Leu Glu Arg Lys Arg Arg Asp
 1               5                  10                  15

His Ile Lys Asp Ser Phe His Ser Leu Arg Asp Ser Val Pro Ser Leu
                20                  25                  30

Gln Gly Glu Lys Ala Ser Arg Ala Gln Ile Leu Asp Lys Ala Thr Glu
            35                  40                  45

Tyr Ile Gln Tyr Thr Gln Gln Lys Val Leu Glu Leu Thr Ser Asp Asn
        50                  55                  60

Asp Arg Leu Arg Lys Arg Val Glu Gln Leu Ser Arg Glu Leu Asp Thr
 65                  70                  75                  80

Leu

<210> SEQ ID NO 64
<211> LENGTH: 81
<212> TYPE: PRT
<213> ORGANISM: Artificial sequence
<220> FEATURE:
<223> OTHER INFORMATION: fusion protein

<400> SEQUENCE: 64

Ala Asp Lys Arg Ala His His Asn Ala Leu Glu Arg Lys Arg Arg Asp
 1               5                  10                  15

His Ile Lys Asp Ser Phe His Ser Leu Arg Asp Ser Val Pro Ser Leu
                20                  25                  30

-continued

```
Gln Gly Glu Lys Ala Ser Arg Ala Gln Ile Leu Asp Lys Ala Thr Glu
         35                  40                  45

Tyr Ile Gln Tyr Ile Gln Gln Lys Val Leu Glu Leu Thr Ser Asp Asn
     50                  55                  60

Asp Arg Leu Arg Lys Arg Val Glu Gln Leu Ser Arg Glu Leu Asp Thr
 65                  70                  75                  80

Leu

<210> SEQ ID NO 65
<211> LENGTH: 4
<212> TYPE: PRT
<213> ORGANISM: Artificial Sequence
<220> FEATURE:
<223> OTHER INFORMATION: fusion protein

<400> SEQUENCE: 65

Met Gln Gln Lys
1

<210> SEQ ID NO 66
<211> LENGTH: 4
<212> TYPE: PRT
<213> ORGANISM: Artificial Sequence
<220> FEATURE:
<223> OTHER INFORMATION: fusion protein

<400> SEQUENCE: 66

Thr Gln Gln Lys
1
```

MINIMALIST BZIP PROTEINS AND USES THEREOF

This application claims the benefit under 35 USC §119(e) of U.S. provisional application No. 60/732,700 filed Nov. 3, 2005.

FIELD OF THE INVENTION

The invention relates to minimalist bZIP proteins and uses thereof. Specifically, the minimalist bZIP proteins are made from the fusion of the basic region of a bHLH protein to the leucine zipper dimerization domain of a bZIP protein. These proteins are particularly useful in treating cancer.

BACKGROUND OF THE INVENTION

Nature's use of the protein α-helix for specific DNA recognition is ubiquitous and maximally utilized by the basic region/leucine zipper motif (bZIP), which comprises a pair of short α-helices that recognize the DNA major groove with sequence-specificity and high affinity (Struhl, K., *Trends Biochem. Sci.* 1989, 14, 137-140; Landschulz, W. H. et al., *Science* 1988, 240, 1759-1764). Crystal structures of the bZIP domain of GCN4 bound to two different DNA sites (König, P. and Richmond, T. J., *J. Mol. Biol.* 1993, 233, 139-154; Ellenberger, T. E. et al., *Cell* 1992, 71, 1223-1237; Keller, W. et al., *J. Mol. Biol.* 1995, 254, 657-667) and the Jun-Fos heterodimer bZIP-DNA crystal (Glover, J. N. M. and Harrison, S. C., *Nature* 1995, 373, 257-261) show that a continuous α-helix of ~60 amino acids provides the basic-region interface for binding to specific DNA sites, as well as the leucine zipper coiled-coil dimerization structure. Remarkably, these crystal structures also demonstrate astonishing conservation of protein backbone structure across species between the two yeast GCN4 and avian Jun-Fos structures.

Myc, Max, and Mad Proteins

The basic-region/helix-loop-helix (bHLH) motif, including the subvariant basic-region/helix-loop-helix/leucine-zipper (bHLHZ) motif, is very similar to the bZIP in that a dimer of α-helices binds specific sites in the DNA major groove; protein dimerization is effected by the helix-loop-helix, a tetramer of α-helices in the bHLH, or by the helix-loop-helix/leucine-zipper in the bHLHZ, in which dimerization is mediated by both the tetrameric HLH and adjacent leucine zipper (compare structures in FIG. 1) (Murre, C. *Cell,* 1989, 56, 777-783). The bHLH comprises bHLH proteins as well as subfamily variants: the bHLHZ (such as Max and USF), and the bHLH/PAS (such as AhR and Arnt), where the PAS domain assists in efficient protein dimerization. Unlike the leucine zipper, the PAS structure is unknown. The PAS has been found in the Per, Arnt, and Sim proteins—hence, "PAS"—as well as AhR and HIF-1α (Gradin, K., et al., *Mol. Cell. Biol.* 1996, 16, 5221-5231). The PAS domain comprises 200-300 amino acids and contains characteristic repeats termed the "A" and "B" domains.

Like bZIP proteins, the bHLH protein family also regulates transcription. In particular, the Myc, Max, and Mad transcription factor network comprises widely expressed bHLHZ proteins critical for control of normal cell proliferation and differentiation (Amati, B. and Land, H., *Curr. Opin. Gene. Dev.* 1994, 4, 102-108; Orian, A. et al., *Genes Dev.,* 2003, 17, 1101-1114). Myc is proto-oncogenic; deregulated overexpression of myc genes leads to malignant transformation, and myc genes are suspected of being among the most frequently affected in human tumors and disease (Nesbit, C. D. et al., *Oncogene* 1999, 18, 3004-3016) including Burkitt's lymphoma (Taub, R. et al., *Proc. Natl. Acad. Sci. USA* 1982, 79, 7837-7841; Dalla-Favera, R. et al., M., *Proc. Natl. Acad. Sci. USA* 1982, 79, 7824-7827), neuroblastomas (Schwab, M. et al., *Nature* 1984, 308, 288-291), and small cell lung cancers (Nau, M. M. et al., *Nature* 1985, 318, 69-73).

In contrast, Max is a stable, constitutively expressed dimerization partner that heterodimerizes with Myc, Mad, and Mxi, thereby controlling their DNA-binding and gene-regulatory activities (Amati, B. and Land, H., *Curr. Opin. Gene. Dev.* 1994, 4, 102-108; Orian, A. et al., *Genes Dev.,* 2003, 17, 1101-1114). Myc-Max is a transcriptional activator that binds the Enhancer box (E-box) sequence 5'-CACGTG (Blackwood, E. M. et al., *Science* 1991, 251, 1211-1217; Blackwell, T. K. et al., *Mol. Cell. Biol.* 1993, 13, 5216-5224). Myc does not homodimerize in vivo or at physiological concentrations, so its activity is mediated by heterodimerization with Max. In contrast Max can homodimerize, although it preferentially heterodimerizes; Max homodimers can bind the E-box, albeit with lower affinities than that of the heterodimers (Blackwood, E. M. et al., *Science* 1991, 251, 1211-1217). Several promoters contain the E-box sequence 5'-CACGTG, including that for p53 tumor suppressor (Reisman, D. et al., *Cell Growth Differ.* 1993, 4, 57-65). Mad-Max (Amati, B. et al., *Cell* 1993, 72, 233-245) and the related Mxi-Max (Zervos, A. S. et al., *Cell* 1993, 72, 223-232) are transcriptional repressors that antagonize Myc-Max by competing for the same E-box sequence.

The Max network is highly conserved in vertebrates and mammals and ubiquitous; in *Drosophila*, for instance, a conservative estimate is that Max network proteins interact with approximately 2000 genes (Orian, A. et al., *Genes Dev.,* 2003, 17, 1101-1114). The transactivation domain mediating the gene-regulatory activities of the Myc-Max heterodimer lies in the amino-terminal region of Myc; Max's role is to allow Myc to bind DNA, thereby mediating its cellular activities (Amati, B. and Land, H., *Curr. Opin. Gene. Dev.* 1994, 4, 102-108). Therefore, mutant proteins that interfere with Myc-Max recognition of the E-box site may also interfere with Myc's disease-promoting activities.

AhR and Arnt Proteins

Not only interesting from a protein-design perspective, the AhR-Arnt system is notable for its possible role in disease pathways. The AhR, also known as the dioxin receptor, mediates signal transduction (Fisher, J. M., et al., *Mol. Carcinogen.* 1989, 1, 216-221) by dioxins and related polycyclic aromatic hydrocarbons, including benzo[a]yrenes found in cigarette smoke and smog, heterocyclic amines in cooked meat, and polychlorinated biphenyls (PCBs). In analogy to the glucocorticoid receptor, the latent AhR is found associated with heat-shock protein hsp90 in the cytosol (Cadepond, F. et al., *J. Biol. Chem.* 1991, 266, 5834-5841.). Ligand binding induces nuclear translocation of the AhR (Pollenz, R. S. et al., *Mol. Pharmacol.* 1995, 45, 428-438), release of hsp90, and dimerization with the nuclear protein Arnt (Reyes, H. et al., *Science* 1992, 256, 1193-1195); this activated complex (Whitelaw, M. et al., *Mol. Cell. Biol.* 1993, 13, 2504-2514; Cuthill, S., et al., *Mol. Cell. Biol.* 1991, 11, 401-411) then binds specific xenobiotic response elements (XRE sites) and activates gene transcription (Wu, L. and Whitlock, J. P. *Nucl. Acid. Res.* 1993, 21, 119-125; Fujisawa-Sehara, A. et al., *Nucl. Acid. Res.* 1987, 15, 4179-4191). The endogenous ligand, if any, for the dioxin receptor has yet to be discovered. During evolution, plant flavones and later, certain combustion products like dioxin, appear to have appropriated the AhR for stimulating their own metabolism.

AhR and Arnt are bHLH/PAS proteins; they differ from most other bHLH transcription factors in that AhR-Arnt dimerization occurs only in the presence of ligand. The PAS domain is remote from the basic region, and importantly, it does not affect DNA binding, as it is purely necessary for dimerization and ligand binding; Poellinger and coworkers found that the minimal bHLH domains of AhR and Arnt are solely capable of recognition of XRE sites and dimerization (Pongratz, I., et al., *Mol. Cell. Biol.* 1998, 18, 4079-4088).

Previous work has shown that within the bZIP family, basic regions and leucine zippers from different proteins can be exchanged with no resulting change in α-helical structure or DNA-binding function (Agre, P. et al., *Science* 1989, 246, 922-926; Lajmi, A. R. et al., *J. Am. Chem. Soc.* 2000, 122, 5638-5639; Sellers, J. W. et al., *Nature* 1989, 341, 74-76). Likewise, the bHLH/bHLHZ is well conserved structurally and essentially identical among bHLH/bHLHZ family members (Nair, S. K. and Burley, S. K., *Cell* 2003, 112, 193-205). Protein-DNA crystal structures for bHLH proteins MyoD (Ma, P. C et al., *Cell* 1994, 77, 451-459) and E47 (Ellenberger, T. et al., *Genes Dev.* 1994, 8, 970-980), and bHLHZ proteins Max (Ferre-D'Amare, A. R. et al., *Nature* 1993, 363, 38-45; Brownlie, P. et al., *Structure* 1997, 5, 509-520) and USF (Ferre-D'Amare, A. R. et al., *EMBO J.* 1994, 13, 180-189) show closely related structures and DNA-binding functions. Exchange of basic regions and dimerization elements in the bHLHZ family also yields native-like proteins: Prochownik and coworkers showed that the Max basic region could be fused to the USF HLHZ domain to generate hybrids that could homodimerize and bind the E-box (Yin, X. et al., *Oncogene* 1998, 16, 2629-2637).

The crystal structures of bZIP and bHLH demonstrate that although they are distinct protein structural families, they share the most similarity in comparison to other families of DNA-binding proteins: in particular, the α-helix DNA recognition element is highly conserved in the two families (König, P. and Richmond, T. J., *J. Mol. Biol.* 1993, 233, 139-154; Ellenberger, T. E. et al., *Cell* 1992, 71, 1223-1237; Keller, W. et al., *J. Mol. Biol.* 1995, 254, 657-667; Glover, J. N. M. and Harrison, S. C., *Nature* 1995, 373, 257-26; Ma, P. C et al., *Cell* 1994, 77, 451-459; Ellenberger, T. et al., *Genes Dev.* 1994, 8, 970-980; Ferre-D'Amare, A. R. et al., *Nature* 1993, 363, 38-45; Brownlie, P. et al., *Structure* 1997, 5, 509-520; Ferre-D'Amare, A. R. et al., *EMBO J.* 1994, 13, 180-189). In contrast, there are differences in the hinge angles which govern positioning of the basic regions in the major grooves between bZIP and bHLH. Additionally, the dimerization element in the bHLH is more complicated than the smaller, simpler leucine zipper.

No simple code exists for protein-DNA recognition, and this fact has made design of sequence-specific DNA-binding proteins a major challenge.

SUMMARY OF THE INVENTION

The invention relates to novel minimalist bZIP proteins that are small, simplified molecular recognition scaffolds. These proteins are useful for design of helical proteins that can target specific DNA ligands.

Accordingly, the invention provides a minimalist bZIP protein comprising:
 a) a basic region of a basic helix-loop-helix protein (bHLH);
 b) a hinge region; and
 c) a leucine zipper domain of a bZIP protein,
 wherein the minimalist bZIP protein binds a target DNA sequence.

The bHLH proteins include bHLH subvariants, bHLHZ subvariants and bHLH/PAS subvariants. In one embodiment, the target DNA sequence is an E-box or XRE1 site.

In a particular embodiment, the invention provides a minimalist bZIP protein comprising:
 a) a basic region from Max;
 b) a hinge region; and
 c) a leucine zipper region from C/EBP,
 wherein the minimalist bZIP protein binds an E-box target DNA sequence.

In another particular embodiment, the invention provides a minimalist bZIP protein comprising:
 a) a basic region from Arnt;
 b) a hinge region; and
 c) a leucine zipper region from C/EBP,
 wherein the minimalist bZIP protein binds an XRE1 target DNA sequence or an E-box target DNA sequence.

In another embodiment, the leucine zipper region in the minimalist bZIP protein is from a synthetic leucine zipper, for example, Lindhout et al. describe a heterodimeric and Hillar et al. describe a homodimeric synthetic leucine zipper. Both of these are de novo, artificial leucine zipper coiled coils (Lindhout D A et al., *Biopolymers,* 2004, 75, 367-75; Hillar et al. *Biochemistry,* 2003, 42, 15710-8).

In yet another particular embodiment, the invention provides for a first and second minimalist bZIP protein comprising a leucine zipper region in the first minimalist bZIP protein and a leucine zipper region in the second minimalist bZIP protein capable of forming a heterodimer. In a specific embodiment, the leucine zipper region in the first minimalist bZIP protein is from Jun and the leucine zipper region in the second minimalist bZIP protein is from Fos.

In yet another embodiment, the minimalist bZIP protein comprises a leucine zipper domain from a different subfamily, for example, the minimalist bZIP protein comprises the basic region of a bHLH/PAS protein, a hinge region and a leucine zipper from a bHLHZ protein.

The invention also provides for the use of the minimalist bZIP proteins of the invention for repressing myc-related transcriptional activation. The invention further provides the use of the minimalist bZIP proteins able to bind to an E-box target DNA sequence for treating cancer. The invention also provides for a method of treating cancer comprising administering an effective amount of a minimalist bZIP protein able to bind to an E-box target DNA sequence to a mammal in need thereof. In one embodiment, the cancer is selected from the group consisting of breast cancer, colon cancer, gynecological cancer, hepatocellular carcinomas, hematological tumors, Burkitt lymphoma, neuroblastoma and small cell lung cancer In another embodiment, the invention provides for the use of the minimalist bZIP proteins able to bind to an XRE1 target DNA sequence for treating cancer. The invention also provides for a method of treating cancer comprising administering an effective amount of a minimalist bZIP protein able to bind to an XRE1 target DNA sequence to a mammal in need thereof. In one embodiment, the cancer is a soft tissue carcinoma or respiratory cancer.

The invention also provides minimalist bZIP proteins further fused to an activation domain, a repressor domain or a drug and uses thereof.

The invention also provides pharmaceutical compositions comprising the minimalist bZIP proteins of the invention and a pharmaceutically acceptable carrier, diluent or excipient, and uses thereof.

Other features and advantages of the present invention will become apparent from the following detailed description. It should be understood, however, that the detailed description

BRIEF DESCRIPTION OF THE DRAWINGS

The invention will now be described in relation to the drawings in which:

FIG. 2 shows Arnt1-C/EBP binding E-box. Plates were grown at 30 deg C. for 6 days. (A) Arnt1-C-EBP inserted into vector pGAD424 and grown on SD-His/-Leu plates with 10 mM 3-AT. (B) Control of vector alone also grown on SD-His/-Leu plates with 10 mM 3-AT.

FIG. 4 shows binding between MM3 and E-box. Plates were incubated four days, 30° C. a. Max/C-EBP plated on SD/-His/-Leu plus 10 mM 3-AT. Binding undetectable (some bubbles arise from sorbitol in plate medium). b. MM3 plated on SD/-His/-Leu plus 10 mM 3-AT. c. MM3 plated on SD/-His/-Leu plus 20 mM 3-AT. d. MM3 plated on SD/-His/-Leu plus 60 mM 3-AT.

FIG. 5 shows the sequence of the hybrid proteins used in investigating the modification of the hinge region. Max bHLHZ components are known from crystal structures; the three highly conserved basic region residues that make sequence-specific contacts to the DNA major groove bases are underlined (His28, Glu32, Arg36) (Ferre-D'Amare A R et al., 1993, Nature 363: 38-45). Arnt bHLH components are putative and based on sequence similarity; Glu98 and Arg102 of Arnt aligning with Glu32 and Arg36 of Max are underlined. The RIR linker is highlighted in bold, black.

FIG. 9 shows sequences of proteins. A) Sequence of original Max-C/EBP hybrid, which comprises the basic region and part of helix 1 of Max (residues 22-47), RIR hinge, and C/EBP leucine zipper (residues 310-338). Sequence of MM10 shows Arg25 mutated to Thr in bold, underline. B) At top is listed the sequence of the native Max bHLHZ (residues 22-113), which served as a positive control. The three highly conserved basic region residues that make sequence-specific contacts to the DNA major groove bases are underlined (His28, Glu32, Arg36). The sequence of the original Max1bHLH-C/EBP template is shown as reference. The non-native RIR hinge linker between the DNA-binding and zipper domains is highlighted in bold, italic. The sequence of the selected MMbHLH/EYR shows the conversion of the original RIR linker to EYR. The first two residues in the C/EBP leucine zipper are highlighted in italic, underline; they differ between the Max1bHLH-C/EBP template and MMbHLH/EYR but should not make a difference in structure or function. In the former, the LE sequence is nonnative and facilitates cloning by providing a Xho I restriction site; this same modification has been used previously in the C/EBP zipper. In the latter, the TQ sequence is native for the C/EBP zipper. Also shown are three further derivatives of MaxbHLH-C/EBP proteins.

DETAILED DESCRIPTION OF THE INVENTION

Figure 1:
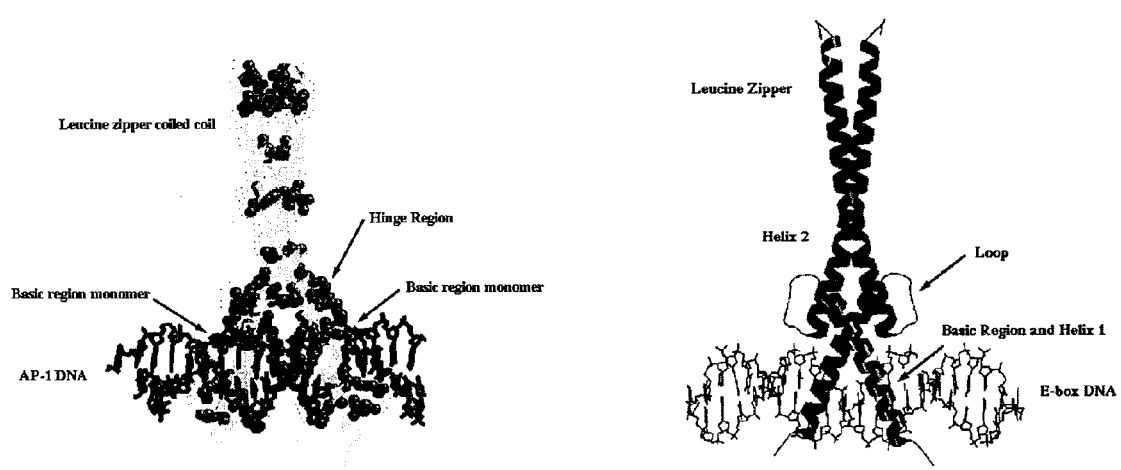
FIG. 1 shows the protein-DNA crystal structure of protein bound to DNA Left. GCN4 bZIP in complex with the AP-1 DNA site, 5'-TGACTCA (Ellenberger, T. E., et al. *Cell*, 1992, 71, 1223-1237). DNA is the dark double helix at the bottom of the figure, and the bZIP is the α-helical dimer above (left). The leucine zipper dimerizes into the coiled-coil, which then smoothly forks to either side of the DNA, allowing the basic region dimer to bind opposite sides of the DNA major groove. Right. Max bHLH/ZIP in complex with the E-box DNA site, 5'-CACGTG (Ferre-D'Amare, A. R., et al. *Nature*, 1993, 363, 38-45). Note that the basic region and helix 1 are contiguous, and that helix 2 and the leucine zipper are contiguous.

The α-helical bZIP motif serves as a manipulable scaffold for protein design. The small, simple bZIP can be a very tractable scaffold for design of new proteins with new DNA recognition properties. The present inventors have examined heterodimeric and homodimeric bZIP motifs in which portions of bHLH and bZIP proteins are fused to create novel hybrid proteins, thus enlarging their binding capabilities. These small proteins still retain the structure and function of native proteins, thus condensing these proteins to minimal units of functionality.

(a) Novel Minimalist bZIP Proteins:

The invention relates to the creation of novel minimalist bZIP proteins based on fusion of the DNA-binding domain from a bHLH protein and the leucine zipper dimerization domain originating from a bZIP protein.

Accordingly, in one embodiment, the invention provides a minimalist bZIP protein comprising a) a basic region of a basic helix-loop-helix protein (bHLH); b) a hinge region; and c) a leucine zipper domain of a bZIP protein, wherein the minimalist bZIP protein binds a target DNA sequence.

In one embodiment, the minimalist bZIP protein of the invention is 30-100 amino acids in length. In a preferred embodiment, the minimalist bZIP protein is 40-60 amino acids in length.

The hinge region offers the minimalist ZIP protein a large amount of flexibility, both in length and identity allowing the protein to best orient itself for binding to the target DNA sequence. The present inventors have shown that variations in the hinge region significantly affects the ability of a minimalist bZIP protein to bind to the target DNA sequence. Technically, a hinge could have zero amino acids, as long as the lengths of basic region and zipper compensate for the flexibility. Alternatively, the hinge could include the entire helix-loop-helix region and/or an additional 0-20 amino acids to provide flexibility similar to the native protein.

Accordingly, in one embodiment, the hinge region has 0-50, preferably 0-20 amino acids. In another embodiment the hinge region has 3-10 amino acids. The amino acids could be any amino acids that affect DNA binding function and maintain proper protein structure. In a specific embodiment, the hinge region comprises the amino acid sequence RIR or GIR. In another specific embodiment, the hinge region comprises the amino acid sequence EYR, MQQK (SEQ ID NO:65) or TQQK (SEQ ID NO:66).

In another embodiment, the hinge region comprises the remainder of the helix-loop-helix of the bHLH protein used for the basic region of the minimalist bZIP protein. In a particular embodiment, the hinge region comprises the remainder of the helix-loop-helix of the bHLH protein used for the basic region of the minimalist bZIP protein and 3-10 amino acids. The amino acids could be any amino acids that affect DNA binding function and maintain proper protein structure, preferably comprising the sequence RIR, GIR, EYR, MQQK (SEQ ID NO:65) or TQQK (SEQ ID NO:66).

The optimal hinge region for a particular minimalist bZIP protein is readily determined by a person skilled in the art using random mutagenesis, i.e. using randomized DNA sequences in the hinge region, for example, randomly mutagenizing a sequence encoding 3-10 amino acids (9-30 bases of DNA). These hinge regions are then incorporated in libraries of minimalist bZIP proteins, the proteins expressed in the yeast one-hybrid system, and selection based on colony survival determined.

The measurement of binding of the minimalist bZIP proteins to the target DNA sequence is a LacZ-based quantitative assay using ortho-nitrophenyl-beta-galactoside as calorimetric substrate (ONPG). Minimalist bZIP proteins with ONPG values exceeding 10 beta-galactosidase units are considered to be good binders to the target DNA sequence. Minimalist bZIP proteins with ONPG values below 10 beta-galactosidase units are ideal for selection and evolution, As the orientation of the minimalist bZIP protein is significant for binding to DNA, each desired minimalist bZIP protein is constructed in triplicate using an additional 1, 2 or 3 amino acids from the C-terminal end of helix 1 in order to select for the best orientation for binding to DNA. One of skill in the art could readily determine which of the 3 hinge regions best orients the protein to the DNA. For example, if the structure is known, this can be analysed by the crystal structure or NMR structure. Alternatively the modeling can be based on the high-resolution structure of a protein known to be similar. Accordingly, in an embodiment of the invention, the invention provides the minimalist bZIP proteins of the invention having an additional 1, 2 or 3 amino acids from the C-terminal end of helix 1 of the bHLH protein between the basic region and the hinge region. A minimalist bZIP protein that does not provide an ideal orientation for DNA binding may be used as a negative control.

The leucine zipper domain is derived from bZIP proteins selected from the group consisting of C/EBP, Jun, Fos, GCN4 and CREB. In another embodiment, the leucine zipper is a synthetic bZIP leucine zipper domain. Where it is desired to construct minimalist bZIP proteins that homodimerize, the preferred leucine zipper domain is derived from C/EBP. Where it is desired to construct minimalist bZIP proteins that heterodimerize, use of the leucine zipper domains of Jun or Fos is preferred.

In one embodiment, the basic region is derived from a bHLH protein selected from the group consisting of a bHLH subvariant, bHLHZ subvariant or bHLH/PAS subvariant. The bHLH subvariant may be selected from the group consisting of MyoD, Myc, E2A, E47, E12, TALL, Id proteins, GL3 and EGL3, TFEB, PIF1, PIL6, ATH, NGN and HAND1. The bHLHZ subvariant may be selected from the group consisting of Mad, Mxi, Max, Myc, Spz1, USF, Mash, BMP, TFE3 and AP4. The bHLH/PAS subvariant may be selected from the group consisting of AhR, Arnt (also known as HIF-1β), HIF-1α, HIF-2α, HIF-3α, Per and Sim.

In a particular embodiment, the bHLHZ subvariant is Max. In another particular embodiment, the bHLH/PAS subvariant is Arnt.

In one embodiment, the minimalist bZIP protein comprises a) a basic region from Max; b) a hinge region; and c) a leucine zipper region from C/EBP, wherein the minimalist bZIP protein binds an E-box target DNA sequence.

In a particular embodiment, the minimalist bZIP protein comprises the amino acid sequence as shown in Table 1 (SEQ ID NOs 1-6), differing only in the number of amino acids in the hinge region.

In another embodiment, the invention provides a minimalist bZIP protein comprising a) a basic region from Arnt; b) a hinge region; and c) a leucine zipper region from C/EBP, wherein the minimalist bZIP protein binds an XRE1 target DNA sequence or an E-box target DNA sequence.

In a particular embodiment, the minimalist bZIP protein comprises the amino acid sequence as shown in Table 2 (SEQ ID NOs 7-12), differing only in the number of amino acids in the hinge region.

In another particular embodiment, the invention provides a minimalist bZIP protein comprising the amino acid sequence as shown in SEQ ID NOs 14-22, 52-54, 56 or 58-64.

In yet another particular embodiment, the invention provides for a first and second minimalist bZIP protein comprising a leucine zipper region in the first minimalist bZIP protein and a leucine zipper region in the second minimalist bZIP protein capable of forming a heterodimer. In a specific embodiment, the leucine zipper region in the first minimalist bZIP protein is from Jun and the leucine zipper region in the second minimalist bZIP protein is from Fos.

The minimalist bZIP proteins of the invention are able to bind target DNA sequences. In one embodiment, the minimalist bZIP proteins bind to the homodimeric E-box DNA sequence 5'-CAG-CTG-3' (Class A proteins) and 5'-CAC-GTG-3' (Class B proteins). In another embodiment, the minimalist bZIP proteins of the invention bind to the heterodimeric XRE1 site 5'-TTGC-GTG-3' (Class C proteins). Class A proteins include MyoD, E47, AP4, E12, Tall and have the consensus as shown in Table 6. Class B proteins include Max, Myc, USF, TFE3, TFEB, Arnt and have the consensus as shown in Table 6 of grant. Class C proteins include AhR and Sim and recognize half sites 5'-T(C/T)GC-3' or 5'-GT(A/G)C-3'. Finally, the minimalist proteins may be generated to heterodimerize with a protein fused to a basic region of a bZIP protein, such as GCN4 which binds to the half site: 5'-TGAC.

The different combinations of basic regions and leucine zipper regions generates a large variety of binding repertoires. The ability to bind to a particular target DNA sequence may depend on the spacing of the target DNA sequences and the flanking sequences found in an endogenous DNA promoter. A person skilled in the art would readily be able to test a minimalist bZIP protein to determine its ability to bind to particular target DNA sequences.

For example, the structure and function of the proteins of the invention can be quantitatively characterized using techniques known in the art, such as by DNase I footprinting; chemical footprinting; circular dichroism; thermodynamics by fluorescence anisotropy and calorimetry; and high-resolution x-ray crystallography and molecular modeling. DNAse I footprinting is used to demonstrate the binding of a protein to a specific DNA sequence. When a protein binds the specific DNA sequence, clear footprints can be seen. A wild type bHLH protein that is expected to bind the sequence can be used as a positive control. Electrophoretic mobility shift assay (EMSA) is a gel assay in which one can detect whether the DNA sequence is bound by the particular protein. If protein binds to the DNA, the DNA's mobility through the gel is retarded, and therefore, the band corresponding to DNA shifts. One can also measure free energies of protein-DNA binding by titrating different concentrations of protein with DNA and measuring the shift. Capillary electrophoresis and other chromatography variants are similar to EMSA gel assay in that free DNA would move through the column matrix differently from DNA bound by protein. Therefore, these assays can measure where free DNA elutes from the matrix; if protein binds DNA, there is a change in mobility of DNA. Normally, protein-bound DNA mobility would be slower. Alternatively, the Yeast two-hybrid or Yeast one-hybrid system can be used to detect DNA-protein interactions as described in the examples section below.

Circular Dichroism is an excellent method for characterizing the structure of bZIP proteins, as the α-helix displays distinctive minima at 208 nm and 222 nm. Fluorescence anisotropy measures the tumbling motion of molecules containing a fluorophore; nanosecond lifetimes of most fluorophores are comparable to the time necessary for rotation of a molecule or complex of molecular weight less than $10^5$ D, the range of many protein-DNA complexes (the excited state fluorescence lifetime for fluorescein is ~4 ns) (Lakowicz, J. R. Principles of Fluorescence Spectroscopy; $2^{nd}$ Edition ed.; Plenum Press: New York, 1999). Large complexes tumble slowly relative to the lifetime of fluorophore and exhibit only slight depolarization of emission with respect to polarized excitation, and a higher anisotropy than small complexes that tumble rapidly (Hill, J. J. and Royer, C. A. "Fluorescence Approaches to Study of Protein-Nucleic Acid Complexation." Meth. Enzymol. 1997, 278, 390-416). Thus, the anisotropy of free, short DNA duplexes should be significantly less than that for the same DNA bound by a protein such as a minimalist bZIP protein of the invention. High-resolution NMR and/or X-ray crystallography for structural characterization would also be useful for characterizing the novel bZIP proteins of the present invention. One can obtain detailed pictures of molecules showing positions of atoms, bond lengths, and distances, producing high-resolution detail of atomic interactions. Calorimetry can also be used for characterization of thermodynamics of complexation. One can measure enthalpies and free energies (and can then calculate entropies) as well as heat capacities. These thermodynamic parameters provide information about how strong the complexation is, how stable it is, how factors like temperature or a mutation or salts can affect the binding strength and stability. Other fluorescence experiments besides anisotropy, including fluorescence resonance energy transfer (FRET) and fluorescence homoquenching can also be used. With FRET and homoquenching, one can label the protein and DNA with fluorophores whose properties are distance-dependent. Therefore, if the fluorophores are close to each other, which would occur when the protein and DNA bind, one would see fluorescence in FRET or would see quenching of fluorescence in homoquenching. Thus, this is useful for detecting binding of the minimalist bZIP protein of the invention with specific target DNA sequences. Mass spectrometry (MS) can be used to determine the molecular weight of the molecule and can even detect molecular complexes, like a protein-DNA complex.

Insertion of alanine residues into the basic region of bZIP has been shown to retain the helical structure and DNA binding of the native protein (Lajmi et al. JACS, 2000, 122, 5638-5639). Accordingly, the minimalist bZIP proteins may be further refined and/or simplified by generating Ala-rich basic regions. The minimalist bZIP proteins may also be strung together such that the helical units can generate multimeric proteins capable of binding longer sequences.

In a further embodiment, the sequences encoding the minimalist bZIP proteins are mutagenized and then the protein products are selected for better binding to the DNA. Accordingly, in one embodiment, the minimalist bZIP proteins are minimalist bZIP proteins of the invention that have been further evolved by mutagenesis and selection. In a particular embodiment, the mutagenesis and the selection occurs in a yeast one-hybrid or yeast two-hybrid system.

In another embodiment, the minimalist bZIP proteins of the invention are fused to an activation domain or a repressor domain. The activation domain may be derived from the proteins Gal4, Myc, Mad (Mxi), and VP16, and HIF-3α. An actual transcriptional repressor is not always necessary for repression of gene expression because if the minimalist bZIP protein sits on a gene or promoter, it may be enough to block or repress the transcription of the gene. However, a repressor may be fused to the minimalist bZIP proteins of the invention. A repressor domain may be derived from Id, Mad (Mxi), and HIF-3α.

The minimalist bZIP proteins of the invention may also contain or be used to obtain or design "peptide mimetics". "Peptide mimetics" are structures which serve as substitutes for peptides in interactions between molecules (See Morgan et al (1989), *Ann. Reports Med. Chem.* 24:243-252 for a review). Peptide mimetics include synthetic structures which may or may not contain amino acids and/or peptide bonds but retain the structural and functional features of the proteins of the invention, including biological activity and a reduced propensity to activate human T cells. Peptide mimetics also include peptoids and oligopeptoids (Simon et al (1972) *Proc. Natl. Acad, Sci USA* 89:9367).

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of the secondary structures of the proteins of the invention. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The molecules of this invention can be prepared in any of several ways but it is most preferably conducted exploiting routine recombinant methods. It is a relatively straightforward procedure to use the protein sequences and information provided herein to deduce a polynucleotide (DNA) encoding any of the preferred protein sequences. This can be achieved for example using computer software tools such as the DNSstar software suite [DNAstar Inc, Madison, Wis., USA] or similar. Any such DNA sequence with the capability of encoding the preferred polypeptides of the present or significant homologues thereof, should be considered as embodiments of this invention.

As a general scheme, genes encoding any of the preferred minimalist bZIP protein sequences can be made using gene synthesis and cloned into a suitable expression vector. In turn the expression vector is introduced into a host cell and cells selected and cultured. The proteins of the invention are purified from the culture medium and formulated into a preparation for therapeutic administration.

Methods for purifying and manipulating recombinant proteins including fusion proteins are well known in the art. Necessary techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

The proteins of the invention can be prepared using recombinant DNA methods. The proteins of the invention may also be prepared by chemical synthesis using techniques well known in the chemistry of proteins such as solid phase synthesis (Merrifield, 1964, *J. Am. Chem. Assoc.* 85:2149-2154) or synthesis in homogenous solution (Houbenweyl, 1987, Methods of Organic Chemistry, ed. E. Wansch, Vol. 15 I and II, Thieme, Stuttgart).

The present invention also provides a purified and isolated nucleic acid molecule comprising a sequence encoding the minimalist bZIP proteins of the invention, preferably a sequence encoding the protein described herein as shown in SEQ ID NOs. 1-12, 14-22, 52, 53 or 54.

The term "isolated and purified" as used herein refers to a nucleic acid substantially free of cellular material or culture medium when produced by recombinant DNA techniques, or chemical precursors, or other chemicals when chemically synthesized. An "isolated and purified" nucleic acid is also substantially free of sequences which naturally flank the nucleic acid (i.e. sequences located at the 5' and 3' ends of the nucleic acid) from which the nucleic acid is derived.

The term "nucleic acid" as used herein refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thio-alkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

In one embodiment, the purified and isolated nucleic acid molecule comprises:

(a) a nucleic acid sequence encoding the amino acid sequences of the proteins of the invention, preferably as shown in SEQ ID NOs. 1-12, 14-22, 52-54, 56 or 58-64;

(b) nucleic acid sequences complementary to (a);

(c) nucleic acid sequences which are homologous to (a) or (b);

(d) a fragment of (a) to (c) that is at least 15 bases, preferably 20 to 30 bases, and which will hybridize to (a) to (c) under stringent hybridization conditions; or (e) a nucleic acid molecule differing from any of the nucleic acids of (a) to (c) in codon sequences due to the degeneracy of the genetic code.

Further, it will be appreciated that the invention includes nucleic acid molecules comprising nucleic acid sequences having substantial sequence homology with the nucleic acid sequences encoding the proteins and peptides of the invention, and fragments thereof. The term "sequences having substantial sequence homology" means those nucleic acid sequences which have slight or inconsequential sequence variations from these sequences, i.e., the sequences function in substantially the same manner to produce functionally equivalent proteins. The variations may be attributable to local mutations or structural modifications.

Nucleic acid sequences having substantial homology include nucleic acid sequences having at least 80%, preferably 90% identity with the nucleic acid sequence encoding the proteins of the invention.

Another aspect of the invention provides a nucleic acid molecule, and fragments thereof having at least 15 bases, which hybridize to nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1-6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

Accordingly, nucleic acid molecules of the present invention having a sequence which encodes a protein of the invention may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

The nucleic acid molecules of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The invention also provides nucleic acids encoding fusion proteins comprising a novel protein of the invention and a selected protein, or a selectable marker protein.

Another aspect of the present invention is a cultured cell comprising at least one of the above-mentioned vectors.

A further aspect of the present invention is a method for preparing a minimalist bZIP protein comprising culturing the above mentioned cell under conditions permitting expression of the minimalist bZIP protein from the expression vector and purifying the minimalist bZIP protein from the cell.

Uses of the Minimalist bZIP Proteins of the Invention:

Mutant proteins that interfere with Myc-Max recognition of the E-box may interfere with Myc's disease promoting activities. Accordingly, the invention provides a use of the minimalist bZIP proteins of the invention able to bind to an E-box target DNA sequence for repressing myc-related transcriptional activation.

Myc is an oncoprotein known to be overexpressed in a wide variety of human diseases, including 80% breast, 70% colon, and 90% gynecological cancers, 50% hepatocellular carcinomas and a variety of hematological tumors (Gardner, L. et al., *Encyclopedia of Cancer*, Bertino, J. R. Ed., 2002, Academic Press).

Accordingly, in one embodiment, the invention provides the use of the minimalist bZIP proteins able to bind to an E-box target DNA sequence for treating cancer. In another embodiment, the invention provides a method of treating cancer comprising administering an effective amount of a minimalist bZIP protein able to bind to an E-box target DNA sequence to a mammal in need thereof. In one embodiment, the cancer is selected from the group consisting of breast cancer, colon cancer, gynecological cancer, hepatocellular carcinomas, hematological tumors, Burkitt lymphoma, neuroblastoma and small cell lung cancer. In another embodiment, the mammal is human.

As discussed above, the minimalist bZIP protein may also be fused to a repressor of transcription. Accordingly, the invention provides the use of a minimalist bZIP protein able to bind to an E-box target DNA sequence fused to a repressor for repressing myc-related transcriptional activation and/or for treating cancer. In another embodiment, the invention provides a method of treating cancer comprising administering an effective amount of a minimalist bZIP protein able to bind to an E-box target DNA sequence fused to a repressor to a mammal in need thereof.

The Myc, Max and Mad transcription factor network are critical for control of normal cell proliferation and differentiation. Accordingly, the invention also provides the use of the minimalist bZIP proteins able to bind to an E-box target DNA sequence for controlling cell proliferation and/or differentiation. In another embodiment, the invention provides the use of a minimalist bZIP protein able to bind to an E-box target DNA sequence fused to an activation domain for activating cell proliferation and/or differentiation. In yet another embodiment, the invention provides the use of a minimalist bZIP protein able to target an E-box target DNA sequence fused to a repressor for repressing cell proliferation and/or differentiation.

In another embodiment, the invention provides for a method of regulating a desired gene by inserting at least one E-box sequence upstream of the desired gene and introducing a minimalist bZIP protein capable of recognizing the inserted E-box sequence, wherein the minimalist bZIP protein then acts to regulate the expression of the gene. The minimalist bZIP protein used in the method can be further fused to an activation or repressor domain.

The Ahr/Arnt system is notable for its possible role in disease pathways given its role in mediating signal transduction by dioxins and related polycyclic aromatic hydrocarbons. Given that the endogenous ligand for the dioxin receptor is not yet known, the minimalist bZIP proteins of the invention that target the XRE1 site are useful for regulating the dioxin pathway.

2,3,7,8-tetrachlorodibenzo-p-dioxin, commonly referred to as TCDD or dioxin, produces a variety of highly toxic effects, including chloracne, teratogenesis, tumor promotion, and immunotoxicity (Whitelaw, M. et al., *Mol. Cell Biol.* 1993, 13, 2504-2514; Poland, A. and Knutson, J. C., *Ann. Rev. Pharmacol. Toxicol.* 1982, 22, 517). Dioxin is an industrial byproduct produced during herbicide manufacture, the bleaching of paper pulp, and combustion of chlorinated organic materials. Dioxin can accumulate in the environment; although it decomposes rapidly in organic solution under artificial or natural light, no photodecomposition occurs in aqueous environments or on wet or dry soil (Crosby, D. G., et al., *Science,* 1971, 173, 748-749). The resistance of dioxin to metabolic degradation and the stability of the dioxin-receptor complex may account for its persistence and toxicity (Johnson, E. F., *Science,* 1991, 252, 924).

Animal studies have proven this ubiquitous pollutant to be extremely lethal, perhaps the most powerful carcinogen tested (Roberts, L., *Science,* 1991, 251, 624-626; Gray, L. E. Jr. and Ostby, J. S., *Toxicol. Appl. Pharmacol.,* 1995, 133, 285-294]. Human effects, however, have been subject to wide controversy, especially in studies concerning dioxin-tainted Agent Orange used by the United States during the Vietnam War as a defoliant.

In 1991, the National Institute of Occupational Safety and Health published an exhaustive examination of 5172 male chemical workers exposed to dioxin on the job from 1942 to 1982 (Fingerhut, M. A., et al., *N. Engl. J. Med.,* 1991, 324, 212-218). The low exposure cohort worked for less than one year in a dioxin-tainted occupation, the high exposure cohort for at least a year; the latency period for cancer occurrence was at least twenty years (Roberts, L., *Science,* 1991, 251, 624-626). The low-exposure group showed no increased risk in cancer, despite exposure to dioxin at levels 90 times higher than that for the general population. The high exposure group, however, was estimated to be exposed to dioxin levels 500 times higher than that for the general population and had nearly a 50% increase in cancer mortality, mostly in soft tissue sarcomas and, unexpectedly, respiratory cancer.

Dioxin's disease/cancerous effects can be mediated by aryl hydrocarbon receptor. This receptor must first bind the ligand to initiate its detrimental effects. A receptor-binding model for dioxin may explain the result that the low-exposure cohort in the NIOSH study discussed above exhibited no increase in cancer risk. Response to dioxin increases slowly at low dioxin concentrations but elevates rapidly after reaching a critical concentration (dissociation constant, $K_d$). Thus, instead of a linear model for dioxin toxicity, the binding curve would be sigmoidal, and there may exist a practical threshold below which dioxin concentrations may be deemed to be "safe." This receptor-mediated mechanism for dioxin action provides a target for monitoring levels of ligand.

The AhR mediates signal transduction by dioxins and related polycyclic aromatic hydrocarbons (PAHs), including benzo[a]pyrenes found in cigarette smoke and smog, heterocyclic amines found in cooked meat, and polychlorinated biphenyls (PCBs) (Fisher, J. M. et al., *Mol. Carcinogen.,* 1989, 1, 216-221). In analogy to the glucocorticoid receptor, the latent dioxin receptor is found associated with heat-shock protein hsp90 in the cytosol (Cadepond, F., et al., *J. Biol. Chem.* 1991, 266, 5834-5831). Ligand binding induces release of hsp90, nuclear translocation of the AhR (Pollenz, R. S., et al., *Mol. Pharmacol.,* 1995, 45, 428-438), and dimerization with the nuclear protein Arnt (Reyes, H., et al., *Science,* 1992, 256, 1193-1195); this activated complex then binds specific DNA sites (xenobiotic response elements or XREs) and activates gene transcription (Wu, L. and Whitlock, J. P. *Nucl. Acid. Res.* 1993, 21, 119-125; Fujisawa-Sehara, A. et al., *Nucl. Acid. Res.* 1987, 15, 4179-4191). Dioxins are very potent inducers of transcription target genes, including cytochrome P450IA1, which codes for aryl hydrocarbon hydroxylase, a catalyst for oxygenation of polycyclic hydrocarbons to phenols and epoxides, some of which are mutagenic and carcinogenic (Whitelaw, M. et al., *Mol. Cell Biol.* 1993, 13, 2504-2514).

Accordingly, the invention also provides the use of a minimalist bZIP protein able to bind to an XRE1 target DNA sequence for treating cancer. In another embodiment, the invention provides a method of treating cancer comprising administering an effective amount of a minimalist bZIP protein able to bind to an XRE1 target DNA sequence to a mammal in need thereof. In another embodiment, the invention provides the use of a minimalist bZIP protein able to bind to an XRE1 target DNA sequence fused to a repressor domain for treating cancer. In yet another embodiment, the invention provides a method of treating cancer comprising administering an effective amount of a minimalist bZIP protein able to bind to an XRE1 target DNA sequence fused to a repressor domain to a mammal in need thereof. In one embodiment, the cancer is a soft tissue carcinoma or respiratory cancer. In another embodiment, the mammal is human.

Since the minimalist bZIP proteins of the invention bind to specific DNA sequences, the proteins may be used as targeting agents. In another embodiment, the minimalist bZIP proteins are fused to a drug. For example, the drug may be an anti-cancer agent. In another embodiment, the invention provides a method of treating cancer comprising administering an effective amount of a minimalist bZIP protein fused to a drug to a mammal in need thereof.

Additionally, these α-helical, bZIP/bHLH hybrids have agricultural and biological (nonhuman) applications. For example, the plant G-box is 5'-CACGTG, the same sequence as the mammalian E-box; the G-box refers specifically to plants. The G-box is bound by bZIP proteins; however, the bZIP/bHLH hybrids of the present invention also bind the G-box, as it is identical to the E-box. Plants use bZIP proteins ubiquitously; *Arabidopsis thaliana* has four times as many bZIP proteins as do humans and yeast (Jakoby, M. et al., *Trends Plant Sci.*, 2002, 7, 106-111). In *Arabidopsis*, many G-box regulated genes are linked to ultraviolet and blue light signal transduction and regulation of light-sensitive promoters, and there is evidence that some GBF-like proteins (G-box binding factor), including ROM1 and ROM1, may regulate storage protein expression, and therefore, play a role in seed maturation. Control of storage protein expression may achieve healthier, more vigorous, larger plants and crops. In addition, the E-box/G-box can be cloned upstream of a gene that one wishes to control: hence, a genetically modified plant. By extension, the genetically modified organism does not have to be a plant, but it could be an animal; these proteins can also have veterinary applications in cases of genes that fortuitously possess an E-box (or E-box-related) or XRE1 (or XRE1-related) sequence in the promoter. This plant could then be engineered to express a bHLH/bZIP hybrid that would then target the cloned E-box/G-box, thereby, regulating the desired gene. Numerous other plant applications are contemplated by the use of minimalist bZIP proteins including controlled regulation of proteins to either enhance or decrease the growth of specific plant organs and tissues by reducing the expression or effectiveness of endogenous growth-associated proteins. The regulation of gene expression by the use of minimalist bZIP proteins and insertions of E-box sequences can result in the modification of various traits, such as durability, size, succulence, texture, and longevity. It is envisioned that both monocotyledonous and dicotyledonous plants can be used, as well as stem and leaf vegetables (e.g., broccoli, lettuce, spinach, cabbage), fruit and seed vegetables (e.g., tomato), fiber crops and cereals (e.g., corn, oats, wheat), and forest and ornamental crops (e.g., cotton). For example, regulation of grape growth in the wine industry in order to provide the ability to fight common grape afflictions, such as phylloxera, or to regulate leaf, root, stem or petiole growth for improved cabbage, spinach, celery, beets, soybeans, sugarcane, flower stalks can be envisioned.

The invention also provides a pharmaceutical composition for treating a mammal with cancer comprising a minimalist bZIP protein of the invention and a pharmaceutically acceptable carrier, diluent or excipient. In a preferred embodiment, the mammal is human. In one embodiment, the minimalist bZIP protein recognizes an E-box/G-box DNA sequence. In a specific embodiment, the cancer is selected from the group consisting of breast cancer, colon cancer, gynecological cancer, hepatocellular carcinomas, hematological tumors, Burkitt lymphoma, neuroblastoma and small cell lung cancer. In another embodiment, the minimalist bZIP protein recognizes an XRE site. In a specific embodiment, the cancer is a soft tissue carcinoma or respiratory cancer. In a further embodiment, the minimalist bZIP protein of the pharmaceutical composition is fused to a repressor.

The proteins of the invention may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of protein to elicit a desired response in the individual. Dosage regime may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, intramuscular, etc.), oral administration, inhalation, transdermal administration (such as topical cream or ointment, etc.), or suppository applications. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences (2000-20th edition) Mack Publishing Company). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Methods of Evolving Better DNA Binding Minimalist bZIP Proteins

In order to examine the binding activities of the minimalist bZIP proteins in vivo, a useful strategy based on the yeast one-hybrid system was used. Examination of in vivo binding was chosen, rather than in vitro, in order to mimic the native cellular environment. Additionally, the system allows for in vivo directed evolution of proteins targeting specific DNA sites: particularly, bZIP-like homodimers that bind the E-box.

An excellent assay for monitoring in vivo interactions between proteins and DNA is provided by the yeast one-hybrid system (Kumar, R. et al., *J. Biol. Chem.*, 1996, 271, 29612-29618; Chen, X. et al., *Nature*, 1996, 383, 691-696). The basis for the yeast one-hybrid assay is the useful fact that eukaryotic transcriptional activators comprise physically and functionally independent DNA-binding domains and activation domains. Therefore, a hybrid protein can be constructed that comprises a DNA-binding domain fused to a suitable transcriptional activator domain. This hybrid can then be assayed for binding to a specific DNA target, because successful protein-DNA complexation results in transcription of one or more reporter genes. Thus, the yeast one-hybrid assay is particularly useful for isolating proteins that bind a specific DNA target; for instance, this system can be used to map the DNA-binding domains of previously known proteins as well as discovery of new proteins capable of recognizing a desired target site.

Because the yeast one-hybrid assay is an in vivo system, it offers the advantage of examination of protein-DNA recognition in the native eukaryotic environment, in contrast to other in vitro surface display technologies (Benhar, I., *Biotech. Adv.*, 2001, 19, 1-33). Both in vivo and in vitro binding assays, such as the yeast one- and two-hybrid assays and phage display, enable monitoring of specific protein-DNA and protein-protein interactions. The main application of such systems is their use for selection of individual targets from large libraries of different clones. Diversity in these libraries can be generated by various means, such as using degenerate oligonucleotides for randomization of large sections of a gene's coding sequence (Wang, B. S. and Pabo, C. O., *Proc. Natl. Acad. Sci. USA,* 1999, 96, 9568-9573) or mutagenic PCR protocols to generate small numbers of random mutations in genes (Cherry, J. R. et al., *Nat. Biotech,* 1999, 17, 379-384). Similarly, a directed evolution process, in which molecules with desired traits can be evolved and isolated, can be achieved by starting with large, diverse libraries of mutants followed by an appropriate selection procedure. Multiple rounds of directed evolution can be performed to give improvement in the desired molecular function.

Creating large libraries of mutant clones can be a tedious and difficult task. This is partially due to the low efficiency of transformation obtained with ligated plasmid vectors-typically one to three orders of magnitude lower transformation efficiency than that obtained with supercoiled plasmids (Tobias, A. V. in *Directed Evolution Library Creation*, Arnold, F. H. and Georgiou, G., Eds, 2003, Humana Press, Totowa, N.J.). An excellent alternative to classical cloning methods involving ligated vectors is cloning by use of homologous recombination (Aylon, Y. and Kupiec, M., *Mut. Res.,* 2004, 566, 231-248). Whereas this method is not applicable in bacteria, due to low frequency of recombination, it is very useful in yeast. In yeast, homologous recombination can substitute for ligation in order to give very high transformation frequencies (Butler, T. and Alcalde, M., in *Directed Evolution Library Creation,* Arnold, F. H. and Georgiou, G., Eds, 2003, Humana Press, Totowa, N.J.). In homologous recombination, mutant gene inserts are cotransformed with linearized plasmid; the end sequences on the inserts and linearized plasmid are homologous. Yeast can then perform homologous recombination on the inserts and plasmids to form closed circular plasmids.

Another advantage is that the homologous recombination procedure also allows the mutated linear PCR products to recombine amongst themselves prior to creation of circular plasmid (Swers, J. S., et al., *Nucl. Acids. Res.,* 2004, 32, 36-44). This process drives shuffling of acquired mutations within the PCR products. Thus, successive rounds of directed evolution using homologous recombination and appropriate selection steps leads to loss of unwanted mutations and accumulation of positive ones—this procedure resembles the natural evolution process.

Accordingly, the minimalist bZIP proteins of the invention can be evolved by:

(a) linearizing DNA duplexes carrying a minimalist bZIP protein sequence;

(b) subjecting the DNA in step (a) to mutagenic PCR to create a mutated minimalist bZIP library;

(c) linearizing an appropriate yeast vector that has anchors homologous with the genes encoded in the minimalize bZIP library in (b);

(d) cotransforming the products of step (c) with the linearized vector into yeast with a genome integrated with target DNA sites; and (e) plating on selective medium;

wherein the colonies that grow in the selective medium have evolved minimalist bZIP proteins that bind to the target DNA site.

The above method can further comprise repeating steps (a) to (e) with the sequence encoding the evolved minimalist bZIP protein.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Generation of Max-C/EBP bZIP Minimalist Proteins

The basic region of Max was fused to the leucine zipper of C/EBP. Three different fusion proteins were constructed Max-1, -2, -3 which differ by one amino acid in order to leave some flexibility in the hinge region—where the zipper is fused to the basic region, which splays out to straddle DNA. Table I shows the sequences of Max-1, -2 and -3-C/EBP with two different hinge regions, RIR and GIR, which are expected to have different helical capabilities. A BamH I site was used for joining the basic regions to the zipper regions. Because there are ~3.5 amino acids per turn in an α-helix, Max-1, -2, and -3 should be sufficient for generating a protein capable of targeting the E-box site. Indeed, the Max-1-C/EBP has been evolved into MM3 which binds to the E-box.

Generation of Arnt-C/EBP bZIP Minimalist Proteins

Arnt is a bHLH protein (no leucine zipper). Arnt basic region binds 5'-GTG, half of the canonical E-box. Native. Arnt preferentially heterodimerizes, but does homodimerize. Three different fusion proteins were constructed Arnt-1, -2, -3 which differ by one amino acid in order to leave some flexibility in the hinge region—where the zipper is fused to the basic region, which splays out to straddle DNA. Table 2 shows the sequences of Arnt-1, -2 and -3-C/EBP with two different hinge regions, RIR and GIR, which are expected to have different helical capabilities.

Design of Protein Heterodimers that Target Asymmetric DNA Site

The xenobiotic response element 1 (XRE1) resides in the 5' flanking region of the CYP1A1 (cytochrome P450) gene. The XRE1 sequence is 5'-TTGC•GTG. Arnt binds to 5'-GTG, which is half of the E-box sequence 5'-CAC•GTG. AhR binds to 5'-TTGC. Fortuitously, well-characterized bHLH and bZIP proteins bind to these same half sites. The bHLH protein Max binds to 5'-CAC•GTG; the bZIP protein C/EBP binds 5'-TTGC•GCM (Agre, P. et al., *Science* 1989, 246, 922-926; Landschulz, W. H. et al., *Science* 1988, 240, 1759-1764). A heterodimer comprising the Max and C/EBP basic regions may therefore recognize 5'-TTGC•GTG, same as the AhR-Arnt heterodimer. Because of the wealth of information on C/EBP and Max, including Max bHLH-DNA crystal structures (Ferre-D'Amare, A. R. et al., *Nature* 1993, 363, 38-45; Ellenberger, T. et al., *Genes Dev.* 1994, 8, 970-980), these proteins were a sound first-generation choice.

We use the leucine zippers from bZIP proteins Jun and Fos to ensure heterodimerization. In the crystal structure (Glover, J. N. M. and Harrison, S. C., *Nature* 1995, 373, 257-261), the Fos-Jun heterodimer is oriented on the AP-1 DNA site (5'-TGACTCA) such that the Fos basic region binds to 5'-TGAC and Jun binds 5'-CTCA. Therefore, the C/EBP basic region is fused to the Fos zipper, whereas the Max basic is fused to the Jun zipper (Table 3). These fusions should maintain proper orientation for heterodimerization such that binding will occur at 5'-TTGC•GTG, rather than 5'-GTG•TTGC. Incidentally, although Jun and Fos preferentially heterodimerize, Jun can homodimerize, whereas Fos does not. Both Max and Arnt can homodimerize, so the Max-Jun and Arnt-Jun homodimers that may occur will be reflective of the natural system.

Second Generation Hybrids: AhR or Arnt Basic Region, Fos or Jun Leucine Zipper

The AhR bHLH is promiscuous in dimerization partners; the AhR bHLH/PAS construct, however, specifically heterodimerizes with only the Arnt bHLH/PAS, and therefore, the PAS domain confers dimerization specificity. The proteins of the invention do not contain the PAS domain, but do use the Jun and Fos leucine zippers to promote heterodimerization.

Hybrids are constructed comprising the basic regions of human AhR (Dolwick, K. M. et al., Mol. Pharm., 1993, 44, 911-917) and human Arnt (Hoffman, E. C., et al., Science, 1991, 252, 954) with the leucine zippers of Fos and Jun, respectively (Table 4). The same flexibility in the fusion junction is explored in these hybrids as well. Thus, portions of Helix 1 in the AhR and Arnt sequences are used to lengthen the hinge between the basic region and zipper. This junction may not be as straightforward as for the well-characterized bHLH proteins used in the first-generation studies, as AhR and Arnt are bHLH/PAS proteins (Hogenesch, J. B. et al., J. Biol. Chem., 1997, 272, 8581-8593; Lindebro, M. C. et al., EMBO J., 1995, 14, 3528-3539), which are closely related, but not identical, to the bHLH and bHLHZ motifs. The reference sequences are shown in Table 5.

Comparison of Protein-DNA Interactions: bHLH, bZIP, and the Unknown AhR

Arnt is believed to form a complex with the 5'-GTG site resembling that of Max, E47, USF, and MyoD—these are all bHLH or bHLHZ proteins that use the same basic-region residues to contact the E-box (Swanson, H. I. and Yang, J.-H., J. Biol. Chem., 1996, 271, 31657-35661). The AhR complex with 5'-TTGC likely represents a unique variant of the bHLH motif; AhR's basic region is unlikely to be strongly helical, as it contains four prolines and one glycine, residues known to be helix breakers (Luque, I. et al., Biochemistry, 1996, 35, 13681-13688). The AhR basic may also not display the characteristic transition from disordered to stable α-helix upon binding to specific DNA, as do other known bHLH proteins (Ferre-D'Amare, A. R. et al., EMBO J. 1994, 13, 180-189).

That the AhR basic may employ a different mechanism from known bHLH proteins for DNA recognition expands the present invention's ability to recognize diverse sequences. Most bZIP and bHLH heterodimers bind half sites that are palindromic or pseudopalindromic. The AhR-Arnt heterodimer binds two distinct, unrelated half sites (Rowlands, J. C. and Gustafsson, J. A., Crit. Rev. Toxicol., 1997, 27, 109-134; Bacsi, S. C. et al., Mol. Pharmacol., 1995, 47, 432-438). Thus, a pair of basic α-helices (or new motifs that AhR represents) is capable of tremendous molecular diversity in ligand-binding.

The Max bHLHZ Structure. The structures of bHLH and bHLHZ proteins in complex with E-box sites show a high level of conservation of specific protein-DNA interactions. The Max bHLH/ZIP complex with the Class B E-box shows three highly conserved specific contacts (Table III): His[28] makes a hydrogen bond to N7 of G3', Glu[32] accepts hydrogen bonds from N4 of C3 and N6 of A2, and Arg[36] makes a hydrogen bond to N7 of G1' at the dyad axis. The intact Max structure also shows the same specific contacts (Brownlie, P. et al., Structure 1997, 5, 509-520), and the USF bHLH/ZIP complex displays these specific contacts and makes equivalent backbone contacts to phosphodiester groups with Asn[29], Arg[33], and Arg[35] as does Max (Ferre-D'Amare, A. R. et al., EMBO J. 1994, 13, 180-189). Both MyoD and E47 are bHLH proteins that bind the Class A E-box. For MyoD, the contacts to the outer base pairs are similar to those of Max: Glu32 accepts hydrogen bonds from N4 of C3 and N6 of A2 (weak, 3.5-3.8 Å distance) (Ma, P. C et al., Cell 1994, 77, 451-459). This essential glutamic acid is absolutely conserved in both Class A and B proteins, and the bifurcated interaction with the CA step is conserved in all structures discussed. E47 makes this same contact with Glu32, plus its side chain methylenes make van der Waals contact with the C5 methyl group on T2' (Ellenberger, T. et al., Genes Dev. 1994, 8, 970-980).

The MyoD bHLH Structure. The other specific contacts that MyoD bHLH makes are not identical to Max bHLH/ZIP: Arg25 makes a hydrogen bond to N7 of G10' and a water-mediated contact to O6 of G10'; Thr29 makes a van der Waals interaction with T2'—the corresponding amino acids in Max and USF do not make specific DNA contacts. Notably, Arg25 is buried in the major groove in MyoD, but in Max, it swings away from the major groove and makes a phosphodiester contact; in its stead, the highly conserved His28 of Max (one helical turn from Arg25) contacts N7 of G3' and displaces the Arg25 side chain. Arg31 of MyoD makes electrostatic contacts with phosphodiesters flanking the E-box and maybe a weak interaction with a flanking adenine; in Class B proteins Max and USF, the corresponding amino acid is hydrophobic and makes no contact at all to DNA. Finally, position 36 is critical for discrimination between the Class A and B E-box sequences. In Class B proteins Max and USF, Arg36 specifically contacts N7 of G1' at the dyad axis. In Class A proteins MyoD and E47, position 36 is occupied by Leu and Val, respectively. Curiously, the MyoD cocrystal structure, shows no contact of Leu36 whatsover with DNA. When Leu36 is mutated to Arg, MyoD now binds to the Class B site. So this position is critical for discrimination of the central base pairs (Blackwell, T. K. et al., Mol. Cell. Biol. 1993, 13, 5216-5224).

Comparison of AhR and Arnt with Known Structures: Swanson and Yang performed extensive mutation and deletion analyses on both the AhR and Arnt basic regions; they show that Arnt behaves similarly to Class B proteins Max and USF (Swanson, H. I. and Yang, J.-H., J. Biol. Chem., 1996, 271, 31657-35661). For Arnt, they found that Glu32, Arg35, and Arg36 were critical for recognition of 5'-GTG, same as Max. They do not discuss His28. When the Glu32 side chain is shortened by mutation to Asp, or when Arg35 and Arg36 are mutated to Gln, DNA binding is abolished, but heterodimerization to AhR is unaffected. When Arg33 and Arg34 are mutated to Gln, DNA-binding is reduced somewhat, so it is likely that these residues are involved in nonspecific phosphodiester interactions, same as for the corresponding amino acids in Max, MyoD, and USF.

Unlike Arnt, AhR does not display classic bHLH behavior. When AhR Pro31 and Ser32 are substituted with Leu and Glu to give a Max-like sequence, binding is abolished. Replacements at Arg34 and Arg36 also virtually abolished DNA-binding. When the two prolines in the AhR sequence KPIPAE (see Table 6) are replaced with alanines, ~70% binding is retained, so these Pro's are not involved in critical interactions. Critical residues for specific DNA binding are Pro31, Ser32, Lys33, Arg34, His35, and Arg36 (Swanson, H. I. and Yang, J.-H., J. Biol. Chem., 1996, 271, 31657-35661). Although AhR is similar to other bHLH and bHLHZ proteins in that it uses the same stretch of amino acids to contact DNA (Table 6), given the four prolines and glycine in its basic region, AhR must be using a nonhelical DNA-binding structure.

How do AhR and Arnt Interact with DNA? The absolutely conserved Asn$^{235}$ of GCN4 spans the major groove to accept a hydrogen bond from N4 of C3' and donate a hydrogen bond to O4 of T4 (Table 6; Asn$^{235}$ of GCN4 is aligned with His$^{28}$ of Max) (Ellenberger, T. E. et al., *Cell* 1992, 71, 1223-1237). This crucial interaction requires that the basic region lie deep in the major groove and specifies two of four base pairs in each half site. GCN4 Asn$^{235}$ corresponds to Max His$^{28}$, as far as comparisons between different protein families can be made. Asn is capable of a bifurcated hydrogen bond and can therefore dictate the identities of two base pairs, and this may explain how bZIP proteins bind a four bp half site, whereas bHLH proteins bind only three bp. In GCN4, the methyl side chains of Ala$^{238}$ and Ala$^{239}$ make van der Waals contacts with the C5 methyl groups on T4 and T2'. The highly conserved Glu$^{32}$ of Max corresponds in position with Ala$^{239}$; Glu32 dictates the outer CA step in Max, much as GCN4 Asn$^{235}$ dictates the outer TG step. Noteworthy is the van der Waals contact that the USF Glu$^{32}$ side chain makes to thymine, akin to that of Ala$^{238}$ and Ala$^{239}$ in GCN4. GCN4 Arg$^{243}$ makes bidentate contact with N7 and O6 of G1' in the AP-1 complex (Ellenberger, T. E. et al., *Cell* 1992, 71, 1223-1237), and N7 of G1' and the phosphodiester group of C1 with ATF/CREB (König, P. and Richmond, T. J., *J. Mol. Biol.* 1993). In bHLHZ proteins, the corresponding Arg$^{36}$ makes a single contact with N7 of the central G, and Leu$^{36}$ in the MyoD bHLH makes no DNA contact. Although the bHLH and bZIP are distinct protein families, their DNA-binding domains display significant similarity in structure and alignment.

Because the bZIP, bHLH, and bHLHZ all use basic α-helical structures to bind the major groove, the corresponding amino acids are similarly placed for DNA-binding function (see alignment in Table 6). Therefore, as long as the basic regions are properly situated in the major groove, α-helical structure and DNA-binding function will be retained. The caveat is to maintain proper orientation for binding; the hinge region is responsible for orienting the basic regions, and therefore flexibility is designed into the hinge by generating variants of each bHLH/bZIP hybrid differing by a single amino acid in the hinge. Although the AhR basic region is unlikely to have substantial helical structure, it is possible that the conserved Asn31 in AhR and Sim may also make a bidentate interaction with DNA, thereby specifying the outer two base pairs. In order to recognize the XRE1 5'-TTGC sequence, Asn31 needs to span the major groove to contact O4 of T4 and N6 of A3' to specify the outer TT step. The inner GC base pairs are recognized by the conserved Lys/Arg34 and Arg37. Although the Class C protein AhR is unlikely to utilize a helical structure to bind the major groove, its basic region contains several conserved amino acids capable of making DNA contacts similar to those discussed for the bHLH and bZIP.

Further Simplification of the Protein Scaffold with Alanine Mutagenesis

Alanine is substituted in the basic region of the minimalist bZIP proteins of the invention (Table 7). Because Arnt is similar to Max and USF, Ala substitutions for Arnt is more straightforward than for AhR, which is not helical, but Ala replacements in AhR should become so.

The Ala-mutants Max-13A, C/EBP-18A, Arnt-16A, and AhR-17A are designed to maintain both specific and nonspecific protein-DNA interactions, akin to the GCN4 mutant 11A; even more heavily mutated proteins are designed wherein only specific contacts are conserved, similar to 18A. In Table 7, specific interactions are boldfaced, nonspecific phosphodiester contacts are underlined, and proposed alanine substitutions are italicized; the Max structure and mutagenesis work on AhR and Arnt are the basis for Table 7 (Ferre-D'Amare, A. R., et al. Nature 1993, 363, 38-45. Swanson, H. I. and Yang, J.-H. J. Biol. Chem. 1996, 271, 31657-31665.) At the bottom of Table 7, the GCN4 sequence is shown as a reference; note that in C/EBP, the highly conserved position 239 is occupied by Val rather than Ala; Val239 is conserved in C/EBP-18A. Most bZIP proteins have Ala239. Johnson has shown that Val239 is an important determinant for C/EBP binding to the half site 5'-TTGC (Johnson, P. F., Mol. Cell. Biol. 1993, 13, 6919-6930). Johnson generated numerous GCN4-C/EBP hybrids wherein the fusion junctions of the two proteins varied; Val239 was critical for discrimination between GCN4 vs. C/EBP sites. Therefore, another mutant would be C/EBP-19A, in which Val239→Ala.

Enlarging the DNA-Binding Repertoire: Determinants of Specificity in bHLH and bHLH/ZIP Proteins Class A proteins target 5'-CAG•CTG, whereas Class B proteins target 5'-CAC•GTG. bHLH proteins MyoD and E47 have highly conserved Arg$^{31}$ and Leu/Val$^{36}$, in contrast to Class B bHLH/ZIP proteins, which contain the absolutely conserved Arg$^{36}$ and a hydrophobic amino acid at position 31 (Leu, Ile, Val, Met—no contact with DNA). MyoD can be changed from Class A to B specificity by mutating Leu$^{36}$ to Arg (Blackwell, T. K. et al., *Mol. Cell. Biol.* 1993, 13, 5216-5224). If Max-13A is a functional Class B protein, then Max-13A-RL may have Class A binding specificity. In this case, Arg$^{31}$ from MyoD is also retained, because it is highly conserved, and the MyoD crystal structure shows that it makes nonspecific interactions with the DNA backbone plus a weak specific contact in the major groove.

These Ala-based minimalist bZIP proteins and the mutants that switch binding between C/EBP and GCN4 or Max and MyoD are tests of the protein-design capabilities of the present invention (Table 8).

Yeast One-Hybrid Assay for Monitoring the In Vivo interactions Between Proteins and DNA Construction of Reporter Strain A reporter strain was constructed such that the E-box target, 5'-CACGTG, resides upstream of the HIS3 reporter gene. The bHLH/bZIP hybrid was fused to the GAL4 transcriptional activation domain so that if a hybrid binds the E-box, the HIS3 protein will be expressed, thus allowing yeast to survive under conditions of histidine auxotrophy. Four tandem copies of the E-box (as shown in Table 9) were cloned into the pHISi-1 integrating reporter vector (Matchmaker One-Hybrid System, Clontech). After insertion of the E-box insert, the pHISi-1 vector was linearized and incorporated into the yeast genome by homologous recombination to generate *Saccharomyces cerevisiae* YM4271[pHISi-1/E-box]. To assess background due to the reporter, 3-aminotriazole (3-AT) was used as a competitive inhibitor of the HIS3 protein. Because it is possible that the reporter may be activated by endogenous factors, YM4271[pHISi-1/E-box] was subjected to titration with varying amounts of 3-AT to measure the concentration of 3-AT sufficient for suppression of background growth. Results demonstrate that 10 mM 3-AT suppresses background expression.

Figure 2:
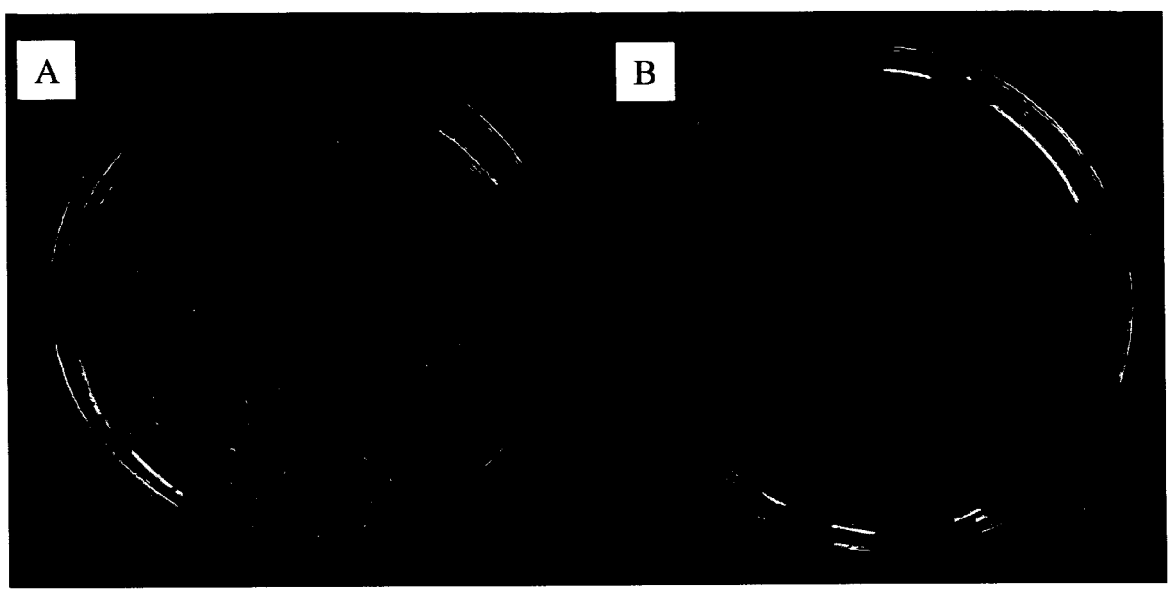

The recombinant plasmid pGAD424 having the Arnt1-C/EBP (SEQ ID NO. 7) insertion was transformed into the reporter strain and plated on SD-His-Leu with 10 mM 3-AT to test for binding activity (FIG. 2A). The vector alone was transformed as a negative control (FIG. 2B). The results show that the Arnt1-C/EBP minimalist bZIP protein was able to bind to the E-box target DNA sequence.

Evolution of the Minimalist bZIP Proteins

Figure 3A:
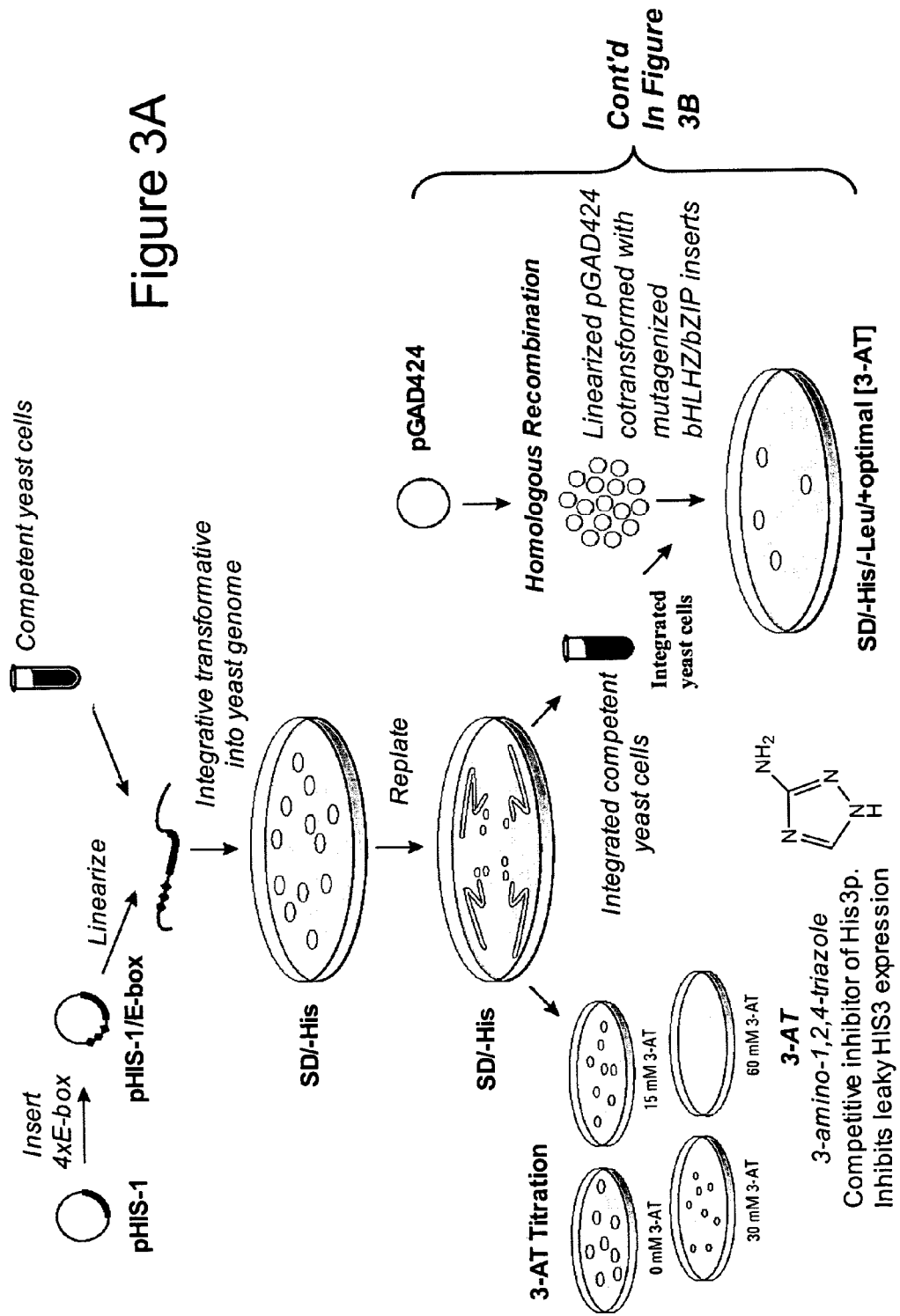
FIG. 3 shows a schematic diagram of the Yeast One Hybrid system used to evolve the minimalist bZIP proteins of the invention.

The minimalist bZIP protein carrying the basic region of Max, a hinge region and the leucine zipper domain of C/EBP was evolved into better binders of the E-box DNA sequence by use of a modified yeast one-hybrid assay, in which mutated PCR fragments were cloned via homologous recombination. A schematic of the process is shown in FIG. 3.

These resultant new protein constructs may compete efficiently with the Myc-Max heterodimer for binding the E-box site and would be therefore able to repress myc transcriptional activity and control the aberrant activity of myc upon oncogenic transformation. Because these fusion proteins do not contain the native Max HLHZ dimerization domain, as it has been replaced by the C/EBP leucine zipper, they are unable to heterodimerize with Myc.

MM3 Protein

Construction of Protein Library

The gene for Max-C/EBP served as the template for mutagenic PCR for generation of the protein library. PCR reaction conditions were adjusted to minimize mutational bias and to yield 1-3 mutations/gene. The mutated Max-C/EBP genes were inserted into vector pGAD424, which carries a GAL4 activation domain and LEU2 selection marker (Matchmaker One-Hybrid System, Clontech).

The original Max-C/EBP hybrid, as shown in Table 10, was tested in the standard yeast one-hybrid assay using the reporter strain described above, and the binding was undetectable. The binding was undetectable likely due to the fact that the E-box used lacks flanking regions and also based on the spacing between the tandem repeats. For example, two other E-box variants, the Max E-box (favored target site for Max) and Arnt E-box (favored target site for Arnt) are also shown in Table 9. Although Max and Arnt both target the core E-box (5'-CACGTG), they have flanking sequence preferences. Additionally, the spacing between the four E-boxes as denoted by $N_{(0, 2, 4, 8)}$ may play a role.

Therefore, the Matchmaker One-Hybrid System from Clontech was modified in order to perform directed evolution. Vector pGAD424 was linearized and cotransformed with an excess of mutagenized Max-C/EBP genes. These mutant PCR products share a 48 base-pair homology with both 5' and 3' ends of the linearized pGAD424 vector. Approximately $10^6$ independent clones were generated during one round of selection.

Library Screening

Transformation of the yeast cells was performed by electroporation. Following electroporation, cells were plated on minimal selective medium lacking leucine and histidine with the appropriate amount of 3-AT to suppress background. Plasmid pGAD424 was also transformed as a negative control; the activation domain alone did not activate the reporter system.

Selection and Validation of Positive Clones

In order to confirm positive clones, that is, those clones expressing protein that bind the DNA target site, a number of validation experiments were performed. Positive colonies indicating potential protein-DNA recognition at the E-box appeared after 4-6 days incubation. Colonies were considered positive if their diameters exceeded 2 mm. Only one grew after replating.

Plasmid DNA from this positive clone was transformed into the control yeast strain containing pHISi-1 plasmid YM4271[pHISi-1], with no integrated target DNA, to test specific binding to E-box. This serves as a negative control to confirm that the selected protein is unable to activate the HIS3 reporter in the absence of target DNA. After successfully passing these two validations, plasmid DNA was sequenced. The sequence is shown in Table 10 as MM3 (mutant Max 3).

The sequence demonstrates that there has been a frameshift resulting in 8 different amino acids in the C-terminal end of the basic region compared to the original Max1-C/EBP minimalist protein sequence. This change would affect spacing and orientation. The changes make sense because they are good alpha-helix formers, one basic residue (R) which is good for making an electrostatic interaction with DNA (maybe far from DNA, but reasonable), and two hydrophilic residues (S and T) that help solubility in water. The sequence also optionally has a mutation in the leucine zipper domain as shown in Table 10.

To reconfirm that the plasmid is truly the source of protein that binds E-box and activates reporter, the sequenced plasmid was again transformed into YM4271[pHISi-1/E-box] and assayed for growth under library screening conditions. Plasmid was extracted from colonies and sequenced a second time. The second sequence matched the first sequence for MM3, thereby confirming the result.

A plasmid containing just the C/EBP leucine zipper was constructed to test the indispensability of the basic region for DNA binding. Although the C/EBP zipper is expected to play some role in aiding DNA binding, for the well-structured, α-helical zipper helps to stabilize the more disordered basic region, the zipper itself is not part of the DNA-binding domain of the bZIP. This control containing just the leucine zipper showed no colony growth as expected.

Figure 4:
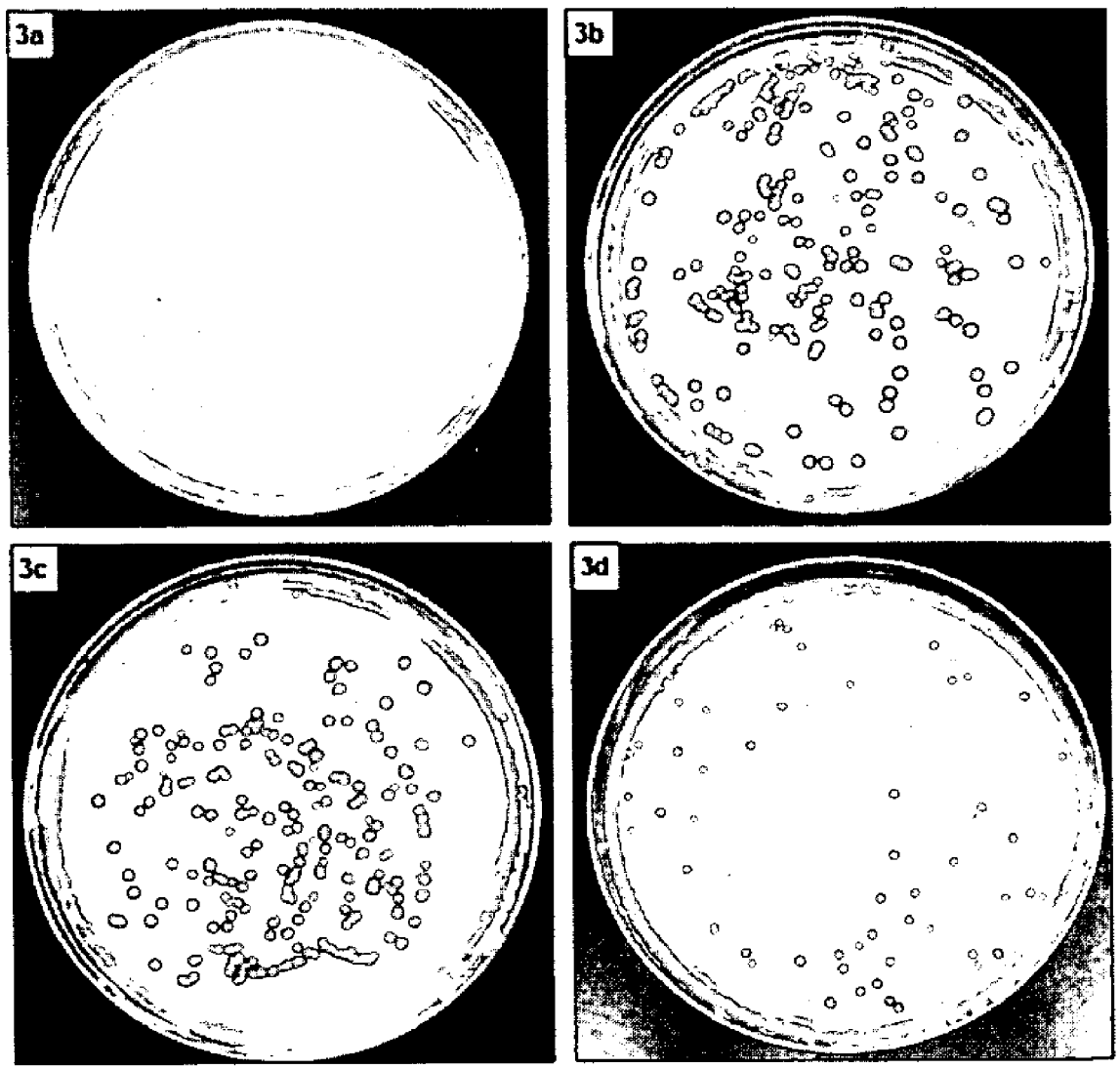

The MM3 is a stronger binder of the E-box than Max-C/EBP (FIG. 4) in this assay; because the Y1H assay is not quantitative, it is not possible to say how strongly MM3 binds E-box. Yeast cells expressing MM3 were plated on plates containing 0-60 mM 3-AT to test the strength of binding between MM3 and E-box. Since 3-AT inhibits HIS3 protein necessary for cell survival under histidine auxotrophy, cell growth on higher concentrations of 3-AT demonstrate strong binding of MM3 to E-box. Even at 60 mM 3-AT, significant colony growth occurs after four days.

MM3 was discovered after only one round of evolution; further evolution may uncover better E-box binding mutants.

Modification of Hinge Region

To elucidate the potential roles of the HLH and PAS domains of Arnt in DNA-binding function and dimerization, three hybrids based on the native Arnt homodimer were designed to target E-box. The mammalian C/EBP zipper was used as the major protein dimerization element, for it is well characterized and forms a strong homodimer (O'Neil, K T et al. 1990, *Science*, 249: 774-778).

The first hybrid, ArntbHLH-C/EBP, comprises the Arnt bHLH domain fused to the C/EBP zipper (FIG. 5); swap of the Arnt PAS for the C/EBP zipper is a dramatic change, for the leucine zipper is one-tenth the size of PAS. Between the bHLH and leucine zipper lies the RIR linker, which provides a BamH I restriction site that facilitates cloning. This construct maintains the alignment of leucines in the C/EBP zipper (Leu/hydrophobic amino acid every seven residues) with Leu142 and Ala135 in Helix 2 of Arnt that may be involved in the hydrophobic interface (numbering same as that for Max, FIG. 5). As the sequence of this construct aligns the hydrophobic leucine dimerization interface with that of the Max bHLHZ, this hybrid was expected to be bHLHZ-like, with a seamless α-helix comprising Helix 2 and leucine zipper as shown in the Max homodimer/E-box crystal structure (Ferre-D'Amare A R et al. 1993, *Nature* 363: 38-45; Brownlie P et al. 1997, *Structure* 5: 509-520). Hence, ArntbHLH-C/EBP is a bHLH/PAS protein converted to bHLHZ.

The second hybrid, ArntbHLH, can dimerize through the HLH domain only, with no zipper or PAS, akin to native bHLH proteins including MyoD (Ma PCM et al., 1994 *Cell* 77: 451-459). Utilizing fluorescence anisotropy, Brennan and coworkers demonstrated that the Arnt bHLH alone (56 amino acids) can bind to E-box under high-salt conditions with $K_d$ value 56.2±11.7 nM. (Huffman, J. L. et al. 2001, *J. Biol. Chem.* 276, 40537). A longer version of the Arnt bHLH domain (142 amino acids, comprises the Arnt bHLH plus the preceding N-terminal region) also shows specific binding to E-box by electrophoretic mobility shift assay (EMSA) (Chapman-Smith A et al. 2004, *J. Biol. Chem.* 279, 5353). The third hybrid, Arnt-C/EBP, contains the Arnt basic region and a portion of Helix 1 directly fused to the C/EBP zipper: this hybrid lacks the HLH and PAS domains, so the leucine zipper is the only dimerization element. Thus, Arnt-C/EBP is a fusion of bHLH/PAS and bZIP to yield a purely α-helical, bZIP-like protein: this hybrid is the most dramatically changed from native Arnt.

Figure 6:
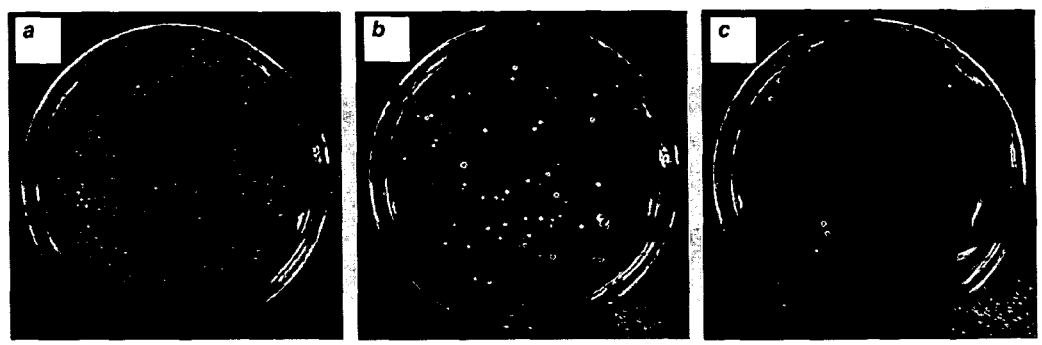
FIG. 6 is an his3 assay. SD/-His/-Leu plates were incubated at 30° C., six days. Note that bubbles arise from sorbitol in plate medium, and glare is visible in the lower right of each photo. a. Positive control Max bHLHZ on 20 mM 3-AT; strong binding/colony growth. b. ArntbHLH-C/EBP on 10 mM 3-AT; strong binding/colony growth. c. ArntbHLH-C/EBP on 20 mM 3-AT; weaker binding/colony growth compared to b.
Figure 7:
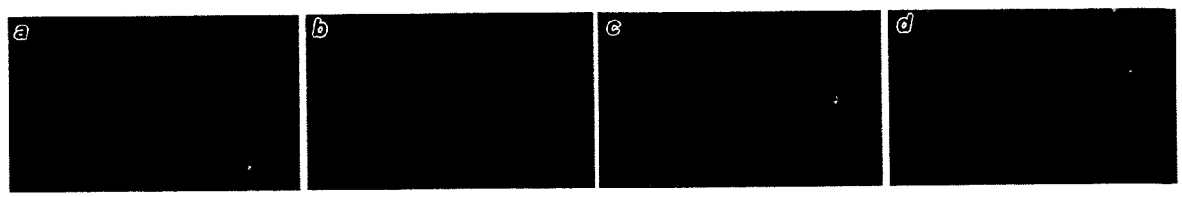
FIG. 7 is a colony-lift filter assay. Note that intensity of blue color is affected by variations in colony size. Color intensity in photos is less vivid than actual plates. a. Positive control Max bHLHZ; positive binding (dark blue). b. ArntbHLH-C/EBP; positive binding (dark blue). c. ArntbHLH; no binding (clear). d. Arnt-C/EBP; no binding (clear).
Figure 8:
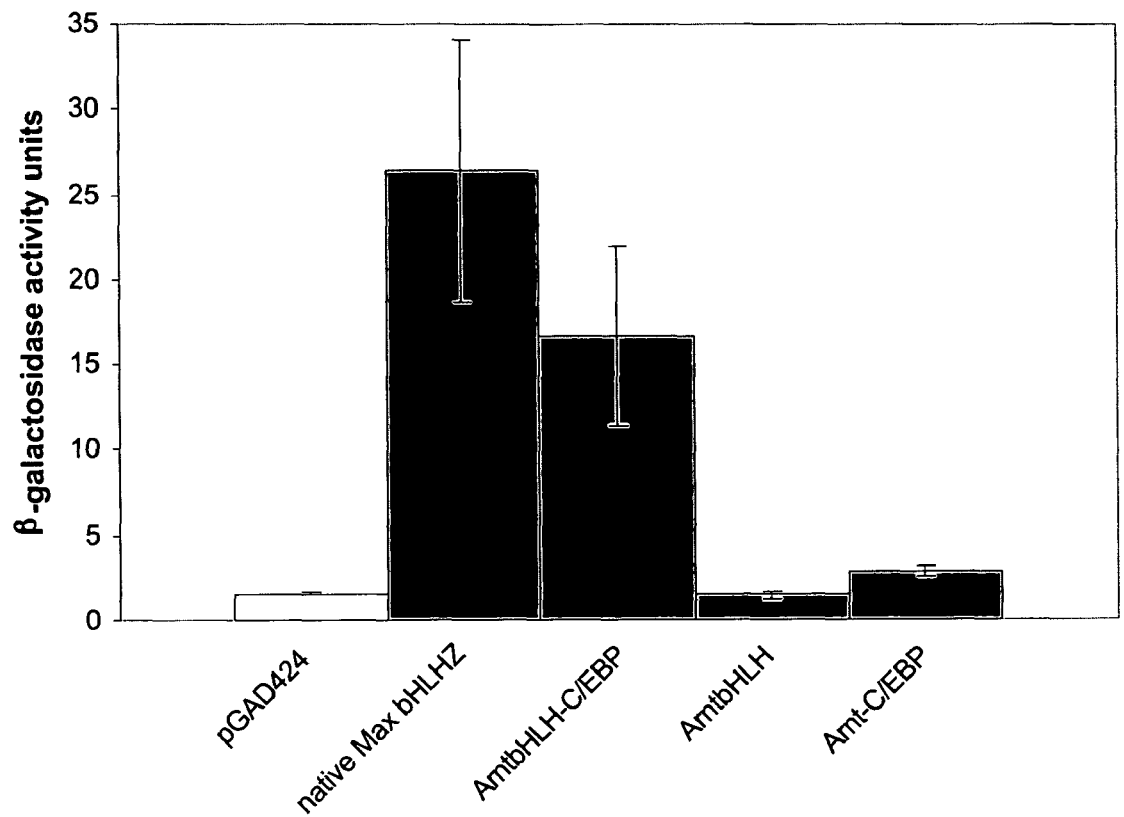
FIG. 8 is a histogram comparing ONPG assay data. All values are the averages of nine to twelve individual measurements from three to four separate cell-growth cultures.

A modified yeast one-hybrid system (Y1H) (Wang MM and Reed RR. 1993, *Nature,* 364, 121) was used to examine the E-box binding activity of the hybrids in vivo. Two *S. cerevisiae* reporter strains were constructed: four tandem copies of the E-box were cloned upstream of either the his3 or LacZ reporters. In the his3 assay, the His3 protein is expressed upon binding of our hybrids at E-box, allowing yeast to survive under histidine auxotrophy (FIG. 6). Surviving colonies are visualized on plates with media lacking histidine and in the presence of 3-aminotriazole (3-AT), a competitive inhibitor of His3 that reduces background growth. Yeast was plated on 10-60 mM 3-AT as a qualitative test of binding strength to E-box. Hybrids were also tested by two assays based on the LacZ reporter, which encodes β-galactosidase. (Serebriiskii, I. G. and Golemis, E. A. 2000 *Anal. Biochem.* 285, 1. The qualitative colony-lift filter assay uses X-gal as substrate for calorimetric visualization of protein-DNA binding (FIG. 7). Positives display vivid blue color. The ortho-nitrophenyl-β-galactoside (ONPG) liquid assay is quantitative (FIG. 8). However, this assay is not sensitive enough to quantify weak interactions accurately, (Mökli, N. and Auerbach, D. 2004 *BioTechniques* 36, 872) so the far more sensitive colony-lift assay is also typically performed.

The native Max bHLHZ control binds well to the E-box in all three assays. The Max bHLHZ (92 amino acids) was used as a positive control, for the minimalist hybrids are more similar in structure and size to the Max bHLHZ. This control gives a strong β-galactosidase activity of 26.4±7.7 (FIG. 8). Likewise, the colony-lift assay shows intense blue color; the his3 assay shows strong colony growth at 20 mM 3-AT (FIGS. 6 and 7), and good colony growth even at 60 mM 3-AT (data not shown). Negative control pGAD424 gives an ONPG reading of 1.6±0.1, with no colony growth by his3 assay and extremely pale color in the colony-lift assay. ArntHLH-C/EBP shows strong β-galactosidase activity of 16.7±5.3 (FIG. 8), comparable to that for native Max bHLHZ. Likewise, his3 colony growth is strong at 20 mM 3-AT, and the colony-lift assay gives bright blue color (FIGS. 6 and 7).

In contrast, the more truncated hybrids showed no detectable binding activity in these assays. Both ArntbHLH and Arnt-C/EBP showed no colony growth on the his3 assay, extremely pale color similar to negative control pGAD424 by colony-lift assay (FIG. 7), and β-galactosidase activities of 1.4±0.3 and 2.9±0.3, respectively (FIG. 8). Interestingly, unlike Brennan and coworkers' (Huffman, J. L. et al. 2004 *J. Biol. Chem.* 276, 40537) and Whitelaw and coworkers' (Chapman-Smith, A. et al. 2004 *J. Biol. Chem.* 279, 5353) in vitro results with the Arnt bHLH, no detectable binding of the Arnt bHLH to E-box was observed by our in vivo Y1H assay. In particular, Brennan and coworkers conducted their in vitro assays under high-salt conditions, and they demonstrated that salt concentration can affect the binding mode and hence, binding affinity. It is possible that the Arnt bHLH alone is not folded properly or becomes unstable in the in vivo environment of yeast.

Additionally, two more derivatives of Arnt-C/EBP were constructed that altered the register of the C/EBP zipper with respect to the Arnt basic region and putative Helix 1: the last Leu112 and Ser113 in Helix 1 were removed in one derivative, and Ser113 removed in the other derivative. Because the α-helix comprises 3.4 amino acids per turn, these three derivatives should provide flexibility in the junction between Arnt and C/EBP to cover all possible orientations of the basic region with regard to the DNA major groove. None of the three derivatives of Arnt-C/EBP exhibited binding to E-box. Thus, it appears that Arnt minimalist bZIP derivatives require modification of the hinge region to optimize DNA-binding.

Thus, the present inventors have shown that using the entire bHLH region of Arnt fused to the C/EBP dimerizing leucine zipper improves binding to the E-box target DNA sequence. In particular, the present inventors have swapped the Arnt PAS (~300 aa) for the C/EBP zipper (~30 aa). Therefore, the much smaller, simpler leucine zipper can substitute for the PAS domain.

Figure 10:
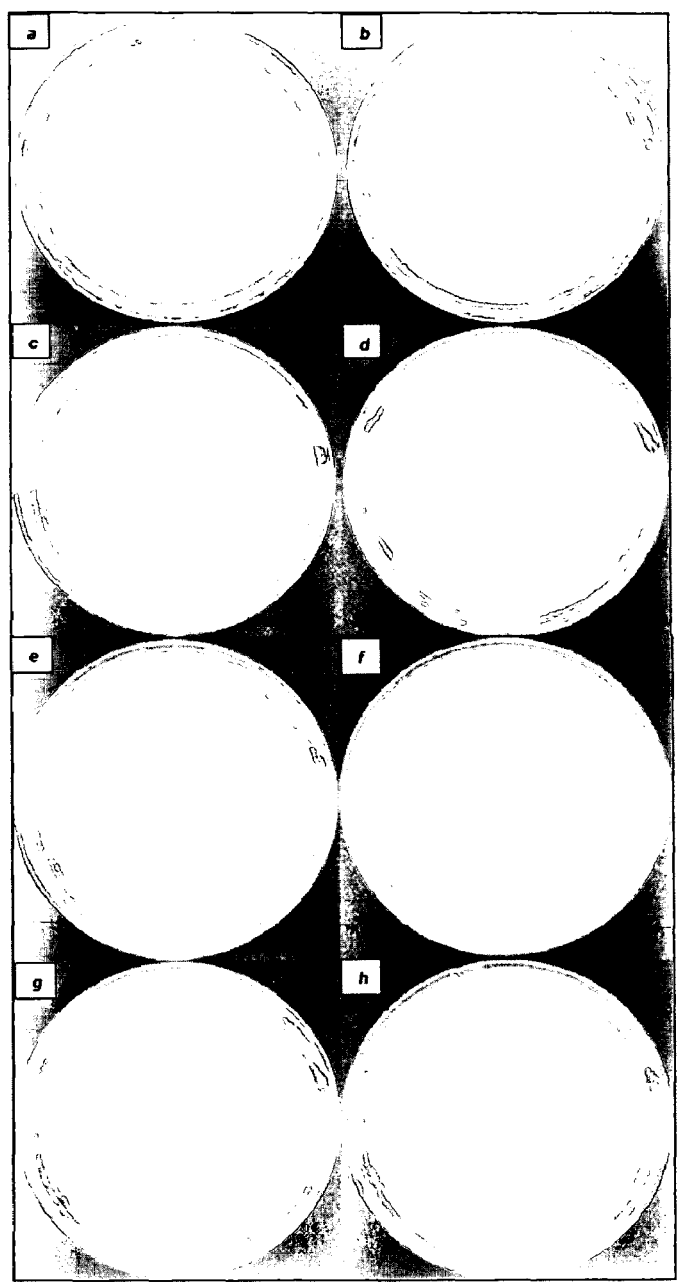
FIG. 10 is an his3 assay. SD/-His/-Leu plates were incubated at 30° C. at specified concentrations of 3-AT; plates were incubated six days in FIGS. 10*a-d*, and five days in FIGS. 10*e-h*. Note that bubbles arise from sorbitol in plate medium. a. Control pGAD424 on 10 mM 3-AT; no binding occurs (two tiny background colonies in northwest corner, bubble in northeast corner). b. Max-C/EBP on 10 mM 3-AT; no binding (several background colonies on lower plate). c. MM10 on 10 mM 3-AT; weak binding/colony growth, some bubbles on mid-lower plate. d. MM10 streaked on 10 mM 3-AT; an average-sized colony from previous plate was streaked to confirm weak, real growth. e. Native Max bHLHZ control on 60 mM 3-AT; strong binding/colony growth. f. Max1bHLH-C/EBP on 10 mM 3-AT; noticeable binding/colony growth. g. Max1bHLH-C/EBP on 60 mM 3-AT; undetectable binding/colony growth, some bubbles. h. MMbHLH/EYR on 60 mM 3-AT; strong binding/colony growth.
Figure 11:
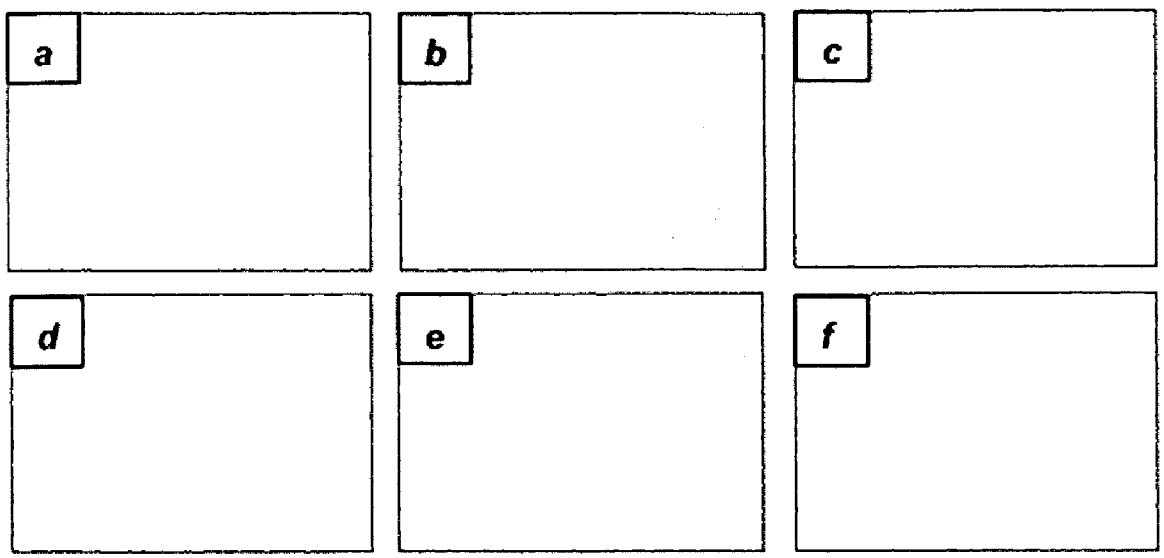
FIG. 11 is a colony-lift filter assay. Note that intensity of blue color is affected by variations in colony size. Color intensity in photo is less vivid than actual plates. a. Control pGAD424; no binding (clear). b. Max-C/EBP; no binding (clear). c. MM10; positive binding (light blue). d. Native Max bHLHZ control; positive binding (dark blue). e. Max1bHLH-C/EBP; positive binding (light blue). f. MMbHLH/EYR; positive binding (dark blue).
Figure 12:
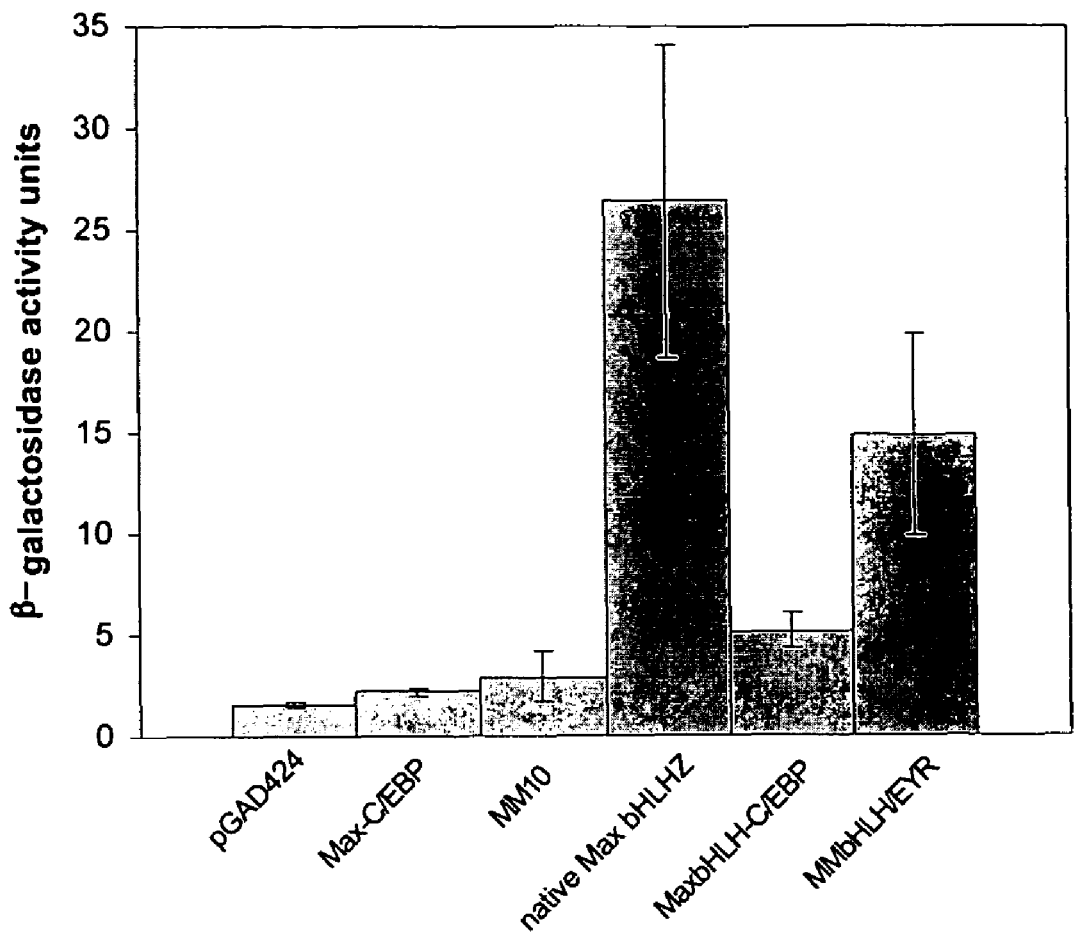
FIG. 12 is a histogram comparing ONPG assay data. Standard deviations are shown as vertical error bars.

Derivatives that contain the Max fused to the C/EBP zipper were made with varying hinge regions, including using the hinge regions having the remainder of the bHLH region of Max and the additional amino acids RIR, EYR, MQQK (SEQ ID NO:65) and TQQK (SEQ ID NO:66) (FIG. 9). The native Max bHLHZ domain was used as the positive control. Some of the derivatives bind E-box significantly better than native Max bHLHZ control. (Tables 11 and 12, FIGS. 10-12) (ONPG TABLE RESULTS 11 and 12)

The tables summarize ONPG values, positive/negative colony growth in yeast cells as assayed by his3 assay on plates, and the LacZ-based X-gal colony-lift filter assay (blue/white screen, very sensitive, but not quantitative). Two different reporters were used, his3 and LacZ, and three types of assays, with the ONPG being quantitative. These data include the native MaxbHLHZ control, MM10, and Max1bHLH-C/EBP (EYR). The results demonstrate that modifying the hinge between the Max basic region and C/EBP zipper significantly increased in DNA-binding function. The original bHLH-RIR hinge region gives an ONPG value of 4.5 whereas replacement of bHLH-RIR with bHLH-EYR gives ONPG 12.

Similar results are expected for modification of hinge regions comprising only the basic region of the bHLH protein. For example, MM10 is a Max basic region directly fused to the C/EBP zipper. It's a very weak binder, for its ONPG is just above baseline but the his3 assay did show weak, consistent colony growth. MM10 has only one mutation, and this was uncovered after one round of selection. The even more truncated proteins can be improved by experimentation with the hinge as it is clear that experimentation with hinge on HLH-containing hybrids helps increase DNA-binding function.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Max basic region, C/EBP leucine zipper (with RIR/GIR linker)

| | | |
|---|---|---|
| Max1-<br>C/EBP<br>(R) | ADKRAHHNALERKRRDHIKDSFHS-RIR-<br>LEQKVLELTSDNDRLRKRVEQLSRELDTL | SEQ ID No. 1 |
| Max2-<br>C/EBP<br>(R) | ADKRAHHNALERKRRDHIKDSFHSL-RIR-<br>LEQKVLELTSDNDRLRKRVEQLSRELDTL | SEQ ID No. 2 |
| Max3-<br>C/EBP<br>(R) | ADKRAHHNALERKRRDHIKDSFHSLR-RIR-<br>LEQKVLELTSDNDRLRKRVEQLSRELDTL | SEQ ID No. 3 |
| Max1-<br>C/EBP<br>(G) | ADKRAHHNALERKRRDHIKDSFHS-GIR-<br>LEQKVLELTSDNDRLRKRVEQLSRELDTL | SEQ ID No. 4 |

TABLE 1-continued

Max basic region, C/EBP leucine zipper (with RIR/GIR linker)

| | | |
|---|---|---|
| Max2-<br>C/EBP<br>(G) | ADKRAHHNALERKRRDHIKDSFHSL-GIR-<br>LEQKVLELTSDNDRLRKRVEQLSRELDTL | SEQ ID No. 5 |
| Max3-<br>C/EBP<br>(G) | ADKRAHHNALERKRRDHIKDSFHSLR-GIR-<br>LEQKVLELTSDNDRLRKRVEQLSRELDTL | SEQ ID No. 6 |

Note:
RIR/GIR spacer added for facile cloning (BamH I site for joining basics and zippers).

TABLE 2

Arnt basic region, C/EBP leucine zipper (with RIR/GIR linker)

| | | |
|---|---|---|
| Arnt1-<br>C/EBP<br>(R) | KFLRCDDDQMSNDKERFARENHSEIERRRRN<br>KMTAYITE-RIR-LEQKVLELTSDNDRLRKR<br>VEQLSRELDTL | SEQ ID No. 7 |
| Arnt2-<br>C/EBP<br>(R) | KFLRCDDDQMSNDKERFARENHSEIERRRRN<br>KMTAYITEL-RIR-LEQKVLELTSDNDRLRK<br>RVEQLSRELDTL | SEQ ID No. 8 |
| Arnt3-<br>C/EBP<br>(R) | KFLRCDDDQMSNDKERFARENHSEIERRRRN<br>KMTAYITELS-RIR-LEQKVLELTSDNDRLR<br>KRVEQLSRELDTL | SEQ ID No. 9 |
| Arnt1-<br>C/EBP<br>(G) | KFLRCDDDQMSNDKERFARENHSEIERRRRN<br>KMTAYITE-GIR-LEQKVLELTSDNDRLRKR<br>VEQLSRELDTL | SEQ ID No. 10 |
| Arnt2-<br>C/EBP<br>(G) | KFLRCDDDQMSNDKERFARENHSEIERRRRN<br>KMTAYITEL-GIR-LEQKVLELTSDNDRLRK<br>RVEQLSRELDTL | SEQ ID No. 11 |
| Arnt3-<br>C/EBP<br>(G) | KFLRCDDDQMSNDKERFARENHSEIERRRRN<br>KMTAYITELS-GIR-LEQKVLELTSDNDRLR<br>KRVEQLSRELDTL | SEQ ID No. 12 |

TABLE 3

First Generation Fusion Proteins: C/EBP or Max basic region, Fos or Jun leucine zipper: Dashes within protein sequences are place holders for sequence alignment purposes. Highly conserved amino acids are in bold. The putative basic helix-loop-helix is marked. The basic regions are aligned at highly conserved positions 32 and 36 using numbering for Max.

| | basic 32 36 / ZIP | SEQ ID No. |
|---|---|---|
| *C/EBP-Fos | SNEYRVRRERNNIAVRKSRDKAKQRNVE---LEAETDQLEDEKSALQTEIANLLKEKEKLEFILAAHRP | 13 |
| Max1-Jun | ADKRAHHNALERKRRDHIKDSFHS---LEEKVKTLKAQNSELASTANMLREQVAQLKQKVMNHVN | 14 |
| Max2-Jun | ADKRAHHNALERKRRDHIKDSFHSL-LEEKVKTLKAQNSELASTANMLREQVAQLKQKVMNHVN | 15 |
| Max3-Jun | ADKRAHHNALERKRRDHIKDSFHSLR-LEEKVKTLKAQNSELASTANMLREQVAQLKQKVMNHVN | 16 |

*replace Q with E in the ZIP for cloning with Xho I enzyme.

TABLE 4

Second Generation Fusion Proteins: AhR or Arnt basic region, Fos or Jun leucine zipper. Dashes within protein sequences are place holders for sequence alignment purposes. Highly conserved amino acids are in bold. The putative basic helix-loop-helix is marked. The basic regions are aligned at highly conserved positions 32 and 36 using numbering for Max.

| | basic 32 36 / ZIP | SEQ ID No. |
|---|---|---|
| AhR1-Fos | ASRKRRKPVQKTVKPIPAEGIKSNPSKRHRDRLNTELDR---LEAETDQLEDEKSALQTEIANLLKEKEKLEFILAAHRP | 17 |
| AhR2-Fos | ASRKRRKPVQKTVKPIPAEGIKSNPSKRHRDRLNTELDRL--LEAETDQLEDEKSALQTEIANLLKEKEKLEFILAAHRP | 18 |
| AhR3-Fos | ASRKRRKPVQKTVKPIPAEGIKSNPSKRHRDRLNTELDRLA-LEAETDQLEDEKALQTEIANLLKEKEKLEFILAAHRP | 19 |
| Arnt1-Jun | KFLRCDDDQMSNDKERFARENHSEIERRRRNKMTAYITE---LEEKVKTLKAQNSELASTANMLREQVAQLKQKVMNHVN | 20 |
| Arnt2-Jun | KFLRCDDDQMSNDKERFARENHSEIERRRRNKMTAYITEL--LEEKVKTLKAQNSELASTANMLREQVAQLKQKVMNHVN | 21 |
| Arnt3-Jun | KFLRCDDDQMSNDKERFARENHSEIERRRRNKMTAYITELS-LEEKVKTLKAQNSELASTANMLREQVAQLKQKVMNHVN | 22 |

*replace Q with E in the ZIP for cloning with Xho I enzyme.

TABLE 5

Reference Sequences: Dashes within protein sequences are place holders for sequence alignment purposes. Highly conserved amino acids are in bold. The putative basic helix-loop-helix is marked.

| | basic / Helix I / loop / Helix II | SEQ ID NO. |
|---|---|---|
| AhR | ASRKRRKPVQKTVKPIPAEGIKSNPSKRHR-DRLNTELDRLASLLPF-PQDVINKLDKL-SVLRLSVTYLRAKSFFDVAL | 23 |
| Arnt | KFLRCDDDQMSNDKERFARENHSEIERRRR-NKMTAYITELSDMVPT-CSALARKPDKL-TILRMAVSHMKSLRGTGNTS | 24 |

| | basic / ZIP | SEQ ID NO. |
|---|---|---|
| Fos | KRRIRRERNKMAAAKCRNRRRELTDT-LQAETDQLEDEKSALQTEIANLLKEKEKLEFILAAHRP | 25 |
| Jun | KAERKRMRNRIAASKCRKRKLERIAR-LEEKVKTLKAQNSELASTANMLREQVAQLKQKVMNHVN | 26 |

TABLE 6

Sequence alignment of basic regions of bHLH, bHLHZ, and bZIP proteins. Numbering is same as that for Max (Ferre-D'Amare, A. R. et al., Nature 1993, 363, 38-45). Highly conserved amino acids are in bold. Adapted from (Swanson, H. I., et al., J. Biol. Chem., 1995, 270, 26292-26302).

| | Basic Regions (Partial) | DNA binding sites | SEQ ID No. |
|---|---|---|---|
| Class B | | | |
| | 25      30 | 321 | |
| Max | ADKRAHHNALERKRR | 5'-CACGTG | 27 |
| Myc | NVKRRTHNVLERQRR | | 28 |
| USF | EKRRAQHNEVERRR | | 29 |
| TFE3 | RQKKDNHNLIERRR | | 30 |
| TFEB | RQKKDNHNLIERRR | | 31 |
| Arnt | RFARENHSEIERRR | | 32 |
| CONSENSUS | --BB--HN--ERRR | | |
| Class A | | | |
| | | 321 | |
| MyoD | ADRRKAATMRERRRL | 5'-CAGCTG | 33 |
| E47 | RERRMANNARERVRV | | 34 |

TABLE 6-continued

Sequence alignment of basic regions of bHLH, bHLHZ, and bZIP proteins. Numbering is same as that for Max (Ferre-D'Amare, A. R. et al., Nature 1993, 363, 38-45). Highly conserved amino acids are in bold. Adapted from (Swanson, H. I., et al., J. Biol. Chem., 1995, 270, 26292-26302).

| | Basic Regions (Partial) | DNA binding sites | SEQ ID No. |
|---|---|---|---|
| AP4 | RIRREIANSNERRRM | | 35 |
| E12 | KERRVANNARERLRV | | 36 |
| Tal1 | VVRRIFTNSRERWRQ | | 37 |
| CONSENSUS | --RR---N-RER-R | | |

Class C

| | | | |
|---|---|---|---|
| | | 4  3  21 | |
| AhR | KPIPAEGIKSNPSKRHRD | 5'-T(C/T)GC half site | 38 |
| Sim | MKEKSKNAARTRRE | 5'-GT(A/G)C half site | 39 |
| CONSENSUS | ------N--B--R- | | | bZIP

| | | 235      4321 | | |
|---|---|---|---|---|
| GCN4 | DPAALKRARNTEAARRSR | 5'-TGAC half site | 40 |

TABLE 7

Alanine-based mutants. Numbering is same as that for Max (Ferre-D'Amare, A. R. et al., Nature 1993, 363, 38-45).

| | Basic      Helix I | |
|---|---|---|
| | 25        30      | | |
| Max | ADKRAHHNALERKRRDHIKDSFHS | SEQ ID NO. 41 |
| Max-13A | AAKRAAHNAAERARRAAAAAAAA | SEQ ID NO. 42 |
| Arnt | KFLRCDDDQMSNDKERLARENH SEIERRRRNKMTAYITE | SEQ ID NO. 43 |
| Arnt-16A | AAARAAHSAAERARRAAAAAAAA | SEQ ID NO. 44 |
| AhR | ASRKRRKPVQKTVKPIPAEGIK SNPSKRHRDRLNTELDR | SEQ ID NO. 45 |
| AhR-17A | AAAAAAAAAPSKRHRAAAAAAAA | SEQ ID NO. 46 | bZIP Sequences

| | 235 | |
|---|---|---|
| C/EBP | SNEYRVRRERNNIAVRKSRDKA KQRNVE | SEQ ID NO. 47 |
| C/EBP-18A | AAAAAAARARNNAAVRKSRAAA AAAAAA | SEQ ID NO. 48 |
| GCN4 | DPAALKRARNTEAARRSRARKL QRMKQ | SEQ ID NO. 49 |

TABLE 8

Alanine-based mutants designed to switch between Class A and Class B binding sites. Numbering is same as that for Max

| | Basic      Helix I | |
|---|---|---|
| | 25    30    | | |
| Max | ADKRAHHNALERKRRDHIKDSFHS | SEQ ID NO. 41 |
| MyoD | ADRRKAATMRERRRLSKVNEAFET | SEQ ID NO. 50 |
| Max-13A | AAKRAAHNAAERARRAAAAAAAA binds 5'-CAC•GTG | SEQ ID NO. 42 |
| Max-13A-RL | AAKRAAHNARERARLAAAAAAAA binds 5'-CAG•CTG | SEQ ID NO. 51 |

TABLE 9

| E-box Inserts | |
|---|---|
| Four Tandem Copies of E-box Insert | 5'-(CACGTG)$_4$-3' |
| Max E-box Insert | 5'-[CCACGTGGN$_{(0,2,6)}$]$_4$-3' |
| Arnt E-box Insert | 5'-[TCACGTGAN$_{(0,2,6)}$]$_4$-3' |

TABLE 10

Evolution of Minimalist bZIP Proteins: Sequence of original Max-C/EBP comprising the basic region of Max, residues 22-47, an RIR linker providing a BamH I site that facilitates cloning, and the C/EBP leucine zipper, residues 310-338. Sequence of MM3 that was evolved after one round of directed evolution in the modified yeast one-hybrid system. Mutations are in bold underline. In the Max basic region, a Leu is mutated to Ser; a frameshift mutation occurs at the C-terminal end of the basic region and in the C/EBP zipper, there is optionally an Asn mutated to Ser.

| Max-C/EBP | ADKRAHHNALERKRRDHIKDSFHS-RIR-LEQKVLELTSDNDRLRKRVEQLSRELDTL | SEQ ID NO. 52 |
|---|---|---|
| MM3a | ADKRAHHNASERKRRDTSRTLSTL-RIR-LEQKVLELTSDSDRLRKRVEQLSRELDTL | SEQ ID NO. 53 |
| MM3b | ADKRAHHNASERKRRDTSRTLSTL-RIR-LEQKVLELTSDNDRLRKRVEQLSRELDTL | SEQ ID NO. 54 |

TABLE 11

Assay Data for Minimalist Proteins

| Protein | his3 | Colony-lift | ONPG[a] |
|---|---|---|---|
| pGAD424 | − | − | 1.6 ± 0.1 |
| Max-C/EBP | − | − | 2.2 ± 0.2 |
| MM10 | + | + | 3.0 ± 1.3 |
| native Max bHLHZ | + | + | 26.4 ± 7.7 |
| Max1bHLH-C/EBP | + | + | 5.2 ± 0.9 |
| MMbHLH/EYR | + | + | 14.8 ± 5.0 |

[a]ONPG values in β-galactosidase units.

TABLE 12

Assay Data for Minimalist Proteins

| Construct | ONPG | No. of samples |
|---|---|---|
| Native Max or MaxbHLHZ | 26.41 ± 7.73 | 3 × 3 = 9 |
| Max-C/EBP (RIR) not in-register | 5.18 ± 0.86 | 3 × 3 + 1 = 10 |
| Max-C/EBP - EYR or MMbHLH/EYR | 14.81 ± 5.01 | 3 × 3 = 9 |
| Max-C/EBP (MQQK) (SEQ ID NO: 65)) | 96.94 ± 20.54 | 4 × 3 = 12 |
| Max-C/EBP (TQQK) (SEQ ID NO: 66)) | 47.46 ± 7.31 | 3 × 3 = 9 |
| Max-C/EBP (IQQK) | 11.53 ± 2.47 | 3 × 3 = 9 |

FULL CITATIONS FOR REFERENCES REFERRED TO IN THE SPECIFICATION

Agre P, Johnson P F, McKnight S L (1989) Cognate DNA binding specificity retained after leucine zipper exchange between GCN4 and C/EBP. Science 246: 922-926.

Amati B, Land H (1994) Myc-Max-Mad: a transcription factor network controlling cell cycle progression, differentiation and death. Curr Opin Gene Dev 4(102-108).

Amati B, Brooks M W, Levy N, Littlewood T D, Evan G I et al. (1993) Oncogenic Activity of the c-Myc Protein Requires Dimerization with Max. Cell 72: 233-245.

Aylon Y, Kupiec M (2004) New insights into the mechanism of homologous recombination in yeast. Mut Res 566(231-248).

Bacsi S G, Reisz-Porszasz S, Hankinson O (1995) Orientation of the Heterodimeric Aryl Hydrocarbon (Dioxin) Receptor Complex on Its Asymmetric DNA Recognition Sequence. Mol Pharmacol 47: 432-438.

Benhar I (2001) Biotechnological applications of phage and cell display. Biotech Adv 19: 1-33.

Blackwell T K, Huang J, Ma A, Kretzner L, Alt F W et al. (1993) Binding of myc proteins to canonical and noncanonical DNA sequences. Mol Cell Biol 13: 5216-5224.

Blackwood E M, Eisenman R N (1991) Max: A Helix-Loop-Helix Zipper Protein That Forms a Sequence-Specific DNA-Binding Complex with Myc. Science 251: 1211-1217.

Brownlie P, Ceska T A, Lamers M, Romier C, Stier G et al. (1997) The crystal structure of an intact human Max-DNA complex: new insights into mechanisms of transcriptional control. Structure 5: 509-520.

Butler T, Alcalde M (2003) Preparing libraries in *Saccharomyces cerevisiae*. In: Arnold F H, Georgiou G, editors. Directed Evolution Library Creation. Totowa, N.J.: Humana Press.

Cadepond F, Schweizer-Groyer G, Segard-Maurel I, Jibard N, Hollenberg S M et al. (1991) Heat Shock Protein 90 as a Critical Factor in Maintaining Glucocorticosteroid Receptor in a Nonfunctional State. J Biol Chem 266: 5834-5841.

Casimiro D R, Wright P E, Dyson H J (1997) PCR-based gene synthesis and protein NMR spectroscopy. Structure 5: 1407-1412.

Casimiro D R, Toy-Palmer A, Blake II R C, Dyson H J (1995) Gene synthesis, high-level expression, and mutagenesis of *Thiobacillus ferrooxidans* rusticyanin: His 85 is a ligand to the blue copper center. Biochemistry 34: 6640-6648.

Chapman-Smith A, Lutwyche J K, Whitelaw M L (2004) Contribution of the Per/Arnt/Sim (PAS) Domains to DNA Binding by the Basic Helix-Loop-Helix PAS Transcriptional Regulators J. Biol. Chem. 279: 5353.

Chen X, Rubock M J, Whitman M (1996) A transcriptional partner for MAD proteins in TGF-β signalling. Nature 383: 691-696.

Cherry J R, Lamsa M H, Scneider P, Vind J, Svendsen A et al. (1999) Directed evolution of a fungal peroxidase. Nat Biotech 17: 379-384.

Crosby D G, Wong A S, Plimmer J R, Woolson E A (1971) Photodecomposition of Chlorinated Dibenzo-p-Dioxins. Science 173: 748-749.

Cuthill S, Wilhelmsson A, Poellinger L (1991) Role of the Ligand in Intracellular Receptor Function: Receptor Affinity Determines Activation In Vitro of the Latent Dioxin Receptor to a DNA-Binding Form. Mol Cell Biol 11: 401-411.

Dalla-Favera R, Bregni M, Erikson J, Patterson D, Gallo R C et al. (1982) Human c-myc oncogene is located on the region of chromosome 8 that is translocated in Burkitt lymphoma cells. Proc Natl Acad Sci USA 79: 7824-7827.

Dolwick K M, Schmidt J V, Carver L A, Swanson H I, Bradfield C A (1993) Cloning and Expression of a Human Ah Receptor cDNA. Mol Pharm 44: 911-917.

Ellenberger T, Fass D, Arnaud M, Harrison S C (1994) Crystal structure of transcription factor E47: E-box recognition by a basic region helix-loop-helix dimer. Genes Dev 8: 970-980.

Ellenberger T E, Brandl C J, Struhl K, Harrison S C (1992) The GCN4 basic region leucine zipper binds DNA as a dimer of uninterrupted a helices: Crystal structure of the protein-DNA complex. Cell 71: 1223-1237.

Ferre-D'Amare A R, Prendergast G C, Ziff E B, Burley S K (1993) Recognition by Max of its cognate DNA through a dimeric b/HLH/Z domain. Nature 363: 38-45.

Ferre-D'Amare A R, Pogonec P, Roeder R G, Burley S K (1994) Structure and function of the b/HLH/Z domain of USF. EMBO J 13: 180-189.

Fingerhut M A, Halperin W E, Marlow D A, Piagitelli L A, Honchar P A et al. (1991) Cancer Mortality in Workers Exposed to 2,3,7,8-Tetrachlorodibenzo-p-dioxin. N Engl J Med 324: 212-218.

Fisher J M, Jones K W, Whitlock J P (1989) Activation of Transcription as a General Mechanism of 2,3,7,8-Tetrachlorodibenzo-p-Dioxin Action. Mol Carcinogen 1: 216-221.

Fujisawa-Sehara A, Sogawa K, Yamane M, Fujii-Kuriyama Y (1987) Characterization of xenobiotic responsive elements upstream from the drug-metabolizing cytochrome P-450c gene: a similarity to glucocorticoid regulatory elements. Nucl Acids Res 15: 4179-4191.

Gardner L, Lee L, Dang C (2002) The c-Myc Oncogenic Transcription Factor. In: Bertino J R, editor. Encyclopedia of Cancer. San Diego, Calif.: Academic Press.

Glover J N M, Harrison S C (1995) Crystal structure of the heterodimeric bZIP transcription factor c-Fos-c-Jun bound to DNA. Nature 373: 257-261.

Gradin K, McGuire J, Wenger R H, Kvietikova I, Whitelaw M L et al. (1996) Functional Interference between Hypoxia and Dioxin Signal Transduction Pathways: Competition for Recruitment of the Arnt Transcription Factor. Mol Cell Biol 16: 5221-5231.

Gray L E J, Ostby J S (1995) In utero 2,3,7,8-tetrachlorodibenzo-p-dioxin (TCDD) alters reproductive morphology and function in female rat offspring. Toxicol Appl Pharmacol 133: 285-294.

Hillar A, Tripet B, Zoetewey D, Wood J M, Hodges R S, Boggs J M. Detection of alpha-helical coiled-coil dimer formation by spin-labeled synthetic peptides: a model parallel coiled-coil peptide and the antiparallel coiled coil formed by a replica of the ProP C-terminus. Biochemistry, 2003, 42, 15170-8.

Hoffman E C, Reyes H, Chu F, Sander F, Conley L H et al. (1991) Cloning of a Factor Required for Activity of the Ah (Dioxin) Receptor. Science 252: 954.

Hogenesch J B, Chan W K, Jackiw V H, Brown R C, Gu Y-Z et al. (1997) Characterization of a Subset of the Basic-Helix-Loop-Helix-PAS Superfamily That Interacts with Components of the Dioxin Signaling Pathway. J Biol Chem 272: 8581-8593.

Huffman J L, Mokashi A, Bachinger H P, Brennan, R G, (2001) The Basic Helix-Loop-Helix Domain of the Aryl Hydrocarbon Receptor Nuclear Transporter (ARNT) Can Oligomerize and Bind E-box DNA Specifically. *J. Biol. Chem.*, 276:40537.

Jakoby M, Weisshaar B, Droge-Laser w, Vicente-Carbajosa J, Tiedemann J et al. (2002) bZIP transcription factors in *Arabidopsis*. Trends Plant Sci 7: 106-111.

Johnson E F (1991) A Partnership between the Dioxin Receptor and a Basic Helix-Loop-Helix Protein. Science 252: 924.

Keller W, König P, Richmond T J (1995) Crystal structure of a bZIP/DNA Complex at 2.2 Å: Determinants of DNA specific recognition. J Mol Biol 254: 657-667.

Kumar R, Chen S, Scheurer D, Wang Q-L, Duh E et al. (1996) The bZIP Transcription Factor Nrl Stimulates Rhodopsin Promoter Activity in Primary Retinal Cell Cultures. J Biol Chem 271: 29612-29618.

König P, Richmond T J (1993) The X-ray structure of the GCN4-bZIP bound to ATF/CREB site DNA shows the complex depends on DNA flexibility. J Mol Biol 233: 139-154.

Lajmi A R, Wallace T R, Shin J A (2000a) Short, Hydrophobic, Alanine-based Proteins Based on the bZIP Motif: Overcoming Inclusion Body Formation and Protein Aggregation During Overexpression, Purification, and Renaturation. Prot Exp Purif 18: 394-403.

Lajmi A R, Lovrencic M E, Wallace T R, Thomlinson R R, Shin J A (2000b) Minimalist, Alanine-based, Helical Protein Dimers Bind to Specific DNA Sites. J Am Chem Soc 122: 5638-5639.

Landschulz W H, Johnson P F, McKnight S L (1988) The Leucine Zipper: A Hypothetical Structure Common to a New Class of DNA Binding Proteins. Science 240: 1759-1764.

Lindebro M C, Poellinger L, Whitelaw M L (1995) Protein-protein interaction via PAS domains: role of the PAS domain in positive and negative regulation of the bHLH/PAS dioxin receptor-Arnt transcription factor complex. EMBO J 14: 3528-3539.

Lindhout D A, Litowski J R, Mercier P, Hodges R S, Sykes B D. NMR solution structure of a highly stable de novo heterodimeric coiled-coil. Biopolymers, 2004, 75, 367-75.

Luque I, Mayorga O L, Freire E (1996) Structure-based thermodynamic scale of α-helix propensities in amino acids. Biochemistry 35: 13681-13688.

Ma P C M, Rould M A, Weintraub H, Pabo C O (1994) Crystal Structure of MyoD bHLH Domain-DNA Complex: Perspectives on DNA Recognition and Implications for Transcriptional Activation. Cell 77: 451-459.

Möckli N, Auerbach D (2004) Quantitative b-galactosidase assay suitable for high-throughput applications in the yeast two-hybrid system *BioTechniques* 36:872.

Murre C, McCaw P S, Baltimore D (1989) A New DNA-Binding and Dimerization Motif in Immunoglobulin Enhancer Binding, daughterless, MyoD, and myc Proteins. Cell 56: 777-783.

Nair S K, Burley S K (2003) X-Ray Structure of Myc-Max and Mad-Max Recognizing DNA: Molecular Bases of Regulation by Proto-Oncogenic Transcription Factors. Cell 112: 193-205.

Nau M M, Brooks B M, Battey J, Sausville E, Gazdar A F et al. (1985) L-Myc, a new Myc-related gene amplified and expressed in human small cell lung cancer. Nature 318: 69-73.

Nesbit C D, Tersak J M, Prochownik E V (1999) MYC oncogenes and human neoplastic disease. Oncogene 18: 3004-3016.

Oliphant A R, Struhl K (1987) The use of random-sequence oligonucleotides for determining consensus sequences. Methods Enzymol 155: 568-582.

Oliphant A R, Nussbaum A L, Struhl K (1986) Cloning of random-sequence oligodeoxynucleotides. Gene 44: 177-183.

O'Neil, K T, Hoess, R H, DeGrado, W F (1990) Design of DNA-Binding Peptides Based on the Leucine Zipper Motif. Science, 249: 774-778.

Orian A, van Steensel B, Delrow J, Bussemaker H J, Li L et al. (2003) Genomic binding by the *Drosophila* Myc, Max, Mad/Mnt transcription factor network. Genes Dev 17: 1101-1114.

Poland A, Knutson J C (1982) 2,3,7,8-Tetrachlorodibenzo-p-dioxin and related halogenated aromatic hydrocarbons: examination of the mechanism of toxicity. Ann Rev Pharmacol Toxicol 22: 517.

Pollenz R S, Sattler C A, Poland A (1995) The Aryl Hydrocarbon Receptor and Aryl Hydrocarbon Receptor Nuclear Translocator Protein Show Distinct Subcellular Localization in Hepa 1c1c7 Cells by Immunofluorescence Microscopy. Mol Pharmacol 45: 428-438.

Pongratz I, Antonsson C, Whitelaw M L, Poellinger L (1998) Role of the PAS Domain in Regulation of Dimerization and DNA Binding Specificity of the Dioxin Receptor. Mol Cell Biol 18: 4079-4088.

Prytulla S, Dyson H J, Wright P E (1996) Gene synthesis, high-level expression and assignment of backbone $^{15}$N and $^{13}$C resonances of soybean leghemoglobin. FEBS Lett 399: 283-289.

Reisman D, Elkind N B, Roy B, Beamon J, Rotter V (1993) c-Myc Transactivates the p53 Promoter through a Required Downstream CACGTG Motif. Cell Growth Differ 4: 57-65.

Reyes H, Reisz-Porszasz S, Hankinson O (1992) Identification of the Ah Receptor Nuclear Translocator Protein (Arnt) as a Component of the DNA Binding Form of the Ah Receptor. Science 256: 1193-1195.

Roberts L (1991) Research News: Dioxin Risks Revisited. Science 251: 624-626.

Rowlands J C, Gustafsson J-Å (1997) Aryl Hydrocarbon Receptor-Mediated Signal Transduction. Crit Rev Toxicol 27: 109-134.

Sambrook J, Fritsch E F, Maniatis T (1989) Molecular Cloning: A Laboratory Manual, 2nd Edition. New York: Cold Spring Harbor Press.

Schwab M, Varmus H E, Bishop J M, Grzeschik K H, Naylor S L et al. (1984) Chromosome localization in normal human cells and neuroblastomas of a gene related to c-Myc. Nature 308: 288-291.

Sellers J W, Struhl K (1989) Changing Fos oncoprotein to a Jun-independent DNA-binding protein with GCN4 dimerization specificity by swapping 'leucine zippers'. Nature 341: 74-76.

Serebriiskii I G, Golemis E A (2000) Uses of lacZ to Study Gene Function: Evaluation of b-Galactosidase Assays Employed in the Yeast Two-Hybrid System. *Anal. Biochem.* 285:1.

Struhl K (1989) Helix-turn-helix, zinc-finger, and leucine-zipper motifs for eucaryotic transcriptional regulatory proteins. Trends Biochem Sci 14: 137-140.

Suga M, Hatakeyama T (2003) High efficiency electroporation by freezing intact cells with addition of calcium. Curr Genet 43(206-211).

Swanson H I, Yang J-H (1996) Mapping the Protein/DNA Contact Sites of the Ah Receptor and Ah Receptor Nuclear Translocator. J Biol Chem 271: 31657-31665.

Swanson H I, Chan W K, Bradfield C A (1995) DNA Binding Specificities and Pairing Rules of the Ah Receptor, ARNT, and SIM Proteins. J Biol Chem 270: 26292-26302.

Swers J S, Kellogg B A, Wittrup K D (2004) Shuffled antibody libraries created by in vivo homologous recombination and yeast surface display. Nucl Acid Res 32: 36-44.

Taub R, Kirsch I, Morton C, Lenoir G, Swan D et al. (1982) Translocation of the c-myc gene into the immunoglobulin heavy chain locus in human Burkitt lymphoma and murine plasmacytoma cells. Proc Natl Acad Sci USA 79: 7837-7841.

Tobias A V (2003) Preparing libraries in *Escherichia coli*. In: Arnold F H, Georgiou G, editors. Directed Evolution Library Creation. Totowa, N.J.: Humana Press.

Wang B S, Pabo C O (1999) Dimerization of zinc fingers mediated by peptides evolved in vitro from random sequences. Proc Natl Acad Sci USA 96: 9568-9573.

Wang M M, Reed R R (1993) Molecular cloning of the olfactory neuronal transcription factor Olf-1 by genetic selection in yeast. *Nature* 364:121.

Whitelaw M, Pongratz I, Wilhelmsson A, Gustafsson J-A, Poellinger L (1993) Ligand-Dependent Recruitment of the Arnt Coregulator Determines DNA Recognition of the Dioxin Receptor. Mol Cell Biol 13: 2504-2514.

Wu L, Whitlock J P (1993) Mechanism of dioxin action: receptor-enhancer interactions in intact cells. Nucl Acid Res 21: 119-125.

Yin X, Grove L, Prochownik E V (1998) Lack of transcriptional repression by max homodimers. Oncogene 16: 2629-2637.

Zervos A S, Gyuris J, Brent R (1993) Mxi1, a Protein hat Specifically Interacts with Max to Bind Myc-Max Recognition Sites. Cell 72: 223-232.

---

The invention claimed is:

1. A minimalist bZIP protein consisting of:
   a) a basic region of a basic helix-loop-helix protein (bHLH);
   b) a hinge region; and
   c) a leucine zipper domain of a bZIP protein,
   wherein the minimalist bZIP protein binds a target DNA sequence.

2. The minimalist bZIP protein of claim 1, wherein the hinge region comprises 0-50 amino acids.

3. The minimalist bZIP protein of claim 2, wherein the hinge region comprises 3 or 4 amino acids.

4. The minimalist bZIP protein of claim 3, wherein the hinge region comprises the sequence RIR or GIR.

5. The minimalist bZIP protein of claim 1, wherein the hinge region further comprises an additional 1, 2, or 3 amino acids derived from the C-terminal end of helix 1 of the bHLH protein between the basic region and the hinge region.

6. The minimalist bZIP protein of claim 1, comprising 30 to 100 amino acids.

7. The minimalist bZIP protein of claim 6, comprising 40 to 60 amino acids.

8. The minimalist bZIP protein of claim 1, wherein the bZIP protein is selected from the group consisting of C/EBP, Jun, Fos, GCN4, and CREB.

9. The minimalist bZIP protein of claim 1, wherein the bHLH protein is selected from the group consisting of a bHLH subvariant, a bHLHZ subvariant, and a bHLH/PAS subvariant.

10. The minimalist bZIP protein of claim 9, wherein the bHLH subvariant is selected from the group consisting of MyoD, Myc, E2A, E47, E12, TALL, Id proteins, GL3, EGL3, TFEB, PIF1, PILE, ATH, NGN, and HAND1.

11. The minimalist bZIP protein of claim 9, wherein the bHLHZ subvariant is selected from the group consisting of Mad, Mxi, Max, Myc, Spz1, USF, Mash, BMP, TFE3, and AP4.

12. The minimalist bZIP protein of claim 9, wherein the bHLH/PAS subvariant is selected from the group consisting of AhR, ARNT, HIF1α, HIF-2α, HIF-3α, Per, and Sim.

13. The minimalist bZIP protein of claim 1, wherein the target DNA sequence is an E-box sequence selected from 5'-CAG CTG and 5'-CAC-GTG.

14. The minimalist bZIP protein of claim 1, wherein the target DNA sequence is an XRE1 sequence 5'-TTGC-GTG.

15. The minimalist bZIP protein of claim 1, wherein the target DNA sequence is a half-site sequence 5'-T(C/T)GC or 5'-GT(A/G)C.

16. The minimalist bZIP protein of claim 1, wherein the basic region of the bHLH protein has been mutated to generate an alanine rich sequence.

17. The minimalist bZIP protein of claim 1, comprising the amino acid sequence as shown in SEQ ID NO: 53.

18. The minimalist bZIP protein of claim 1 comprising the amino acid sequence as shown in SEQ ID NO: 54.

19. The minimalist bZIP protein of claim 1, wherein the basic region is from Max, the leucine zipper region is from C/EBP, and the target DNA sequence is an E-box sequence.

20. The minimalist bZIP protein of claim 19, comprising an amino acid sequence selected from the sequences as shown in SEQ ID NOs: 1-6.

21. The minimalist bZIP protein of claim 1, wherein the basic region is from Arnt, the leucine zipper region is from C/EBP and the target DNA sequence is an XRE1 target DNA sequence.

22. The minimalist bZIP protein of claim 21, comprising an amino acid sequence selected from the sequences as shown in SEQ ID NOs: 7-12.

23. The minimalist bZIP protein of claim 1, wherein the protein is further fused to an activation domain.

24. The minimalist bZIP protein of claim 23, wherein the activation domain is derived from Gal4, Mad, Myc, and VP16.

25. The minimalist bZIP protein of claim 1, wherein the protein is further fused to a drug for drug delivery.

26. The minimalist bZIP protein of claim 1, wherein the protein is further fused to a repressor domain.

27. The minimalist bZIP protein of claim 26, wherein the repressor domain is Mxi, Id, and HIF-3α.

28. The minimalist bZIP protein of claim 1 comprising the amino acid sequence as shown in SEQ ID NOs: 14-22, 52-54, 56, or 58-64.

29. A minimalist bZIP protein heterodimer comprising a first and second minimalist bZIP protein comprising a leucine zipper region in the first minimalist bZIP protein and a leucine zipper region in the second minimalist bZIP protein capable of forming a heterodimer; wherein the first minimalist bZIP protein and the second minimalist bZIP protein each consist of:
   a) a basic region of a basic helix-loop-helix protein (bHLH);
   b) a hinge region; and
   c) a leucine zipper domain of a bZIP protein.

30. The minimalist bZIP protein heterodimer of claim 29, wherein the leucine zipper region in the first minimalist bZIP protein is from Jun and the leucine zipper in the second minimalist bZIP protein is from Fos.

31. A pharmaceutical composition comprising the minimalist bZIP protein of claim 1 and a pharmaceutically acceptable carrier, diluent or excipient.

* * * * *